United States Patent
Fischell et al.

(10) Patent No.: US 12,306,187 B2
(45) Date of Patent: May 20, 2025

(54) APPARATUS AND METHODS USING TETHERED ENZYMES FOR THE DETECTION OF THE ENZYMATIC ACTIVITY OF BIOMARKERS

(71) Applicant: TETmedical, Inc., Fair Haven, NJ (US)

(72) Inventors: David R. Fischell, Fair Haven, NJ (US); Roy Cohen, Cortland, NY (US); Alexander J. Travis, Ithaca, NY (US); Furkat Mukhtarov, Ithaca, NY (US); John Mcguire Jaicks, Alexandria, VA (US)

(73) Assignee: TETmedical, Inc., Fair Haven, NJ (US)

(*) Notice: Subject to any disclaimer, the term of this patent is extended or adjusted under 35 U.S.C. 154(b) by 0 days.

(21) Appl. No.: 18/390,083

(22) Filed: Dec. 20, 2023

(65) Prior Publication Data

US 2024/0218422 A1  Jul. 4, 2024

Related U.S. Application Data

(60) Provisional application No. 63/477,700, filed on Dec. 29, 2022.

(51) Int. Cl.
| | | |
|---|---|---|
| *C12Q 1/52* | (2006.01) | |
| *A61J 1/05* | (2006.01) | |
| *C12Q 1/527* | (2006.01) | |
| *G01N 21/76* | (2006.01) | |
| *G01N 33/543* | (2006.01) | |
| *G01N 33/573* | (2006.01) | |

(52) U.S. Cl.
CPC .............. *G01N 33/573* (2013.01); *A61J 1/05* (2013.01); *C12Q 1/52* (2013.01); *C12Q 1/527* (2013.01); *G01N 21/76* (2013.01); *G01N 33/54346* (2013.01); *G01N 2333/91188* (2013.01); *G01N 2333/988* (2013.01); *G01N 2800/28* (2013.01)

(58) Field of Classification Search
CPC ......... C12N 11/18; C12N 11/02; C12N 11/14; C12N 9/0063; C12N 9/0006; C12N 9/0048; C12Y 110/03003; C12Y 101/03004; C12Y 107/03003; G01N 2333/90206; G01N 2333/902
See application file for complete search history.

(56) References Cited

U.S. PATENT DOCUMENTS

| | | | | |
|---|---|---|---|---|
| 5,213,765 A | * | 5/1993 | Kasai | ................... G01N 33/491 436/178 |
| 9,547,014 B2 | * | 1/2017 | Travis | ................... C12N 11/18 |

FOREIGN PATENT DOCUMENTS

| JP | WO2003021255 | * 12/2004 |
|---|---|---|

OTHER PUBLICATIONS

Mapungwana et al. "The effect of fructose on pyruvate kinase activity in isolated hepatocytes" Biochem. J. (1982) 208, 171-178 (Year: 1982).*
Promega "Steady-Glo® Luciferase Assay System" 10 page Jul. 2013 (Year: 2013).*
Sigma Aldrich "Pyruvate Kinase Activity Assay Kit" 4 pages 2012 (Year: 2012).*

* cited by examiner

Primary Examiner — Thane Underdahl
(74) Attorney, Agent, or Firm — Rosenberg, Klein & Lee

(57) ABSTRACT

A coupled enzyme reaction point of care assay system detects and measures an active enzyme biomarker from a patient's blood sample. The assay system has a point of care blood collector for collecting blood into a blood collection vial. A biomarker detection mechanism has at least three fluid flow entities. Each fluid flow entity has a fluid input zone and a corresponding reaction zone. The fluid flow entities include a test strip, a negative control strip and a positive control strip. The reaction zones include components from a multiplicity of substrates, co-factors, buffers and cryoprotectants, and a multiplicity of tethered enzymes. At least one of the tethered enzymes is an enzyme that produces luminescence. The tethered enzymes are adapted to react to a constituent which may be a biomarker. A photonic luminescence reader measures light emitted from an active enzyme biomarker present in the patient's blood.

13 Claims, 20 Drawing Sheets

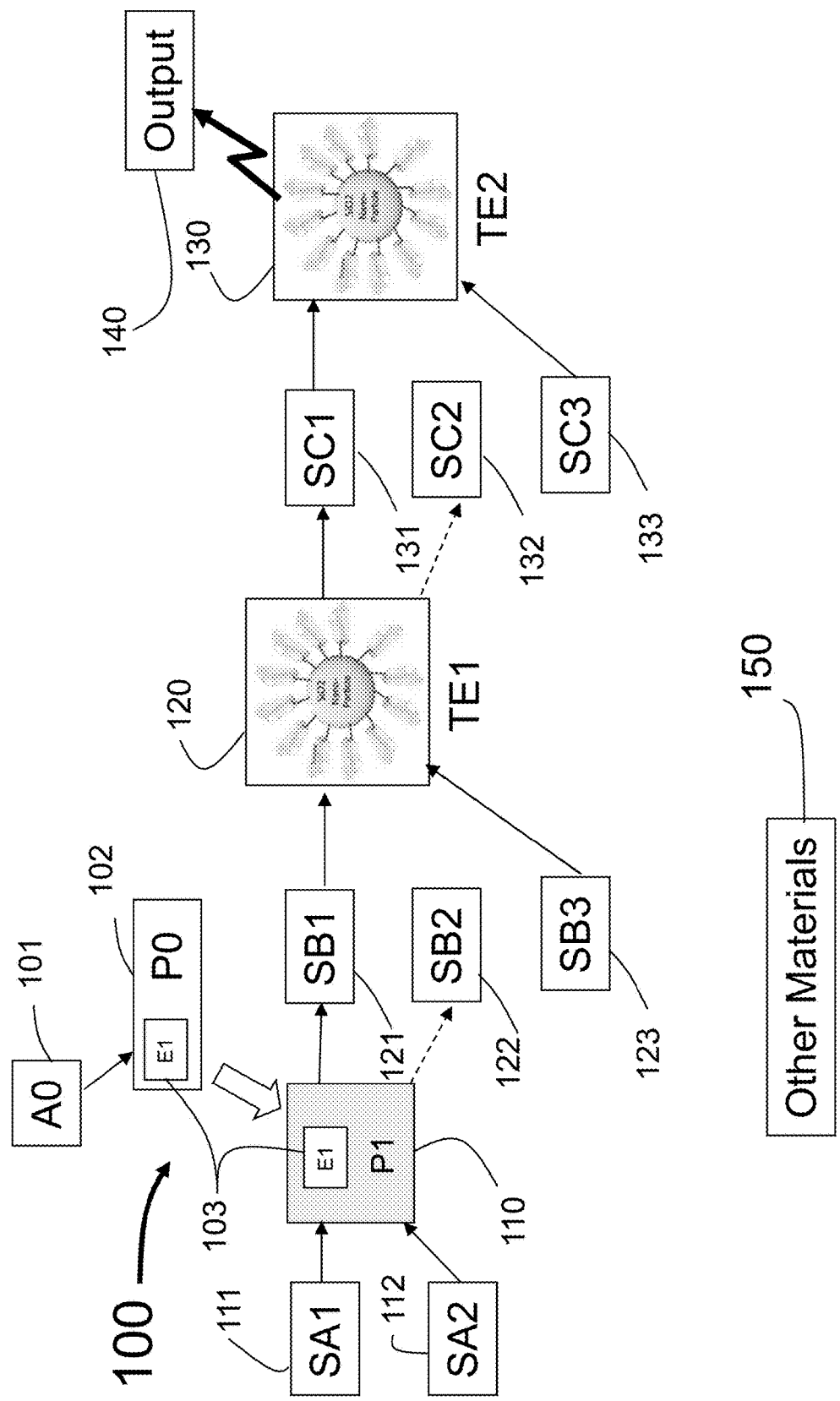
FIG. 1 – Three Step TET Enzyme Assay

| Component | NSE-FA | Liver Enzyme ALT | Liver Enzyme AST |
|---|---|---|---|
| P0 - 102 | Plasma/Serum | Plasma/Serum | Plasma/Serum |
| A0 - 101 | | TET-Uricase & Uric Acid | TET-Uricase & Uric Acid |
| E1 - 110 | Plasma with NSE-FA | Plasma/Serum with ALT | Plasma/Serum with AST |
| SA1 - 111 | 2-PG | α-ketoglutarate | α-ketoglutarate |
| SA2 - 112 | PEP | L-Alanine | L-Aspartate |
| SB1 (made by biomarker) -121 | ADP | Glutamate | Glutamate |
| SB2 - 122 | | Pyruvate | Oxaloacetate |
| SB3 - 123 | TET-PK | | |
| TE1 - 120 | ATP | TET-Glut-Ox | TET-Glut-Ox |
| SC1 (made by TE1) – 131 | Luciferin | $H_2O_2$ | $H_2O_2$ |
| SC3 - 133 | TET-Luciferase | Luminol | Luminol |
| TE2 - 130 | | TET-HRP | TET-HRP |
| Output Signal - 140 | Photons | Photons | Photons |

FIG. 2 – Table of Assay Components

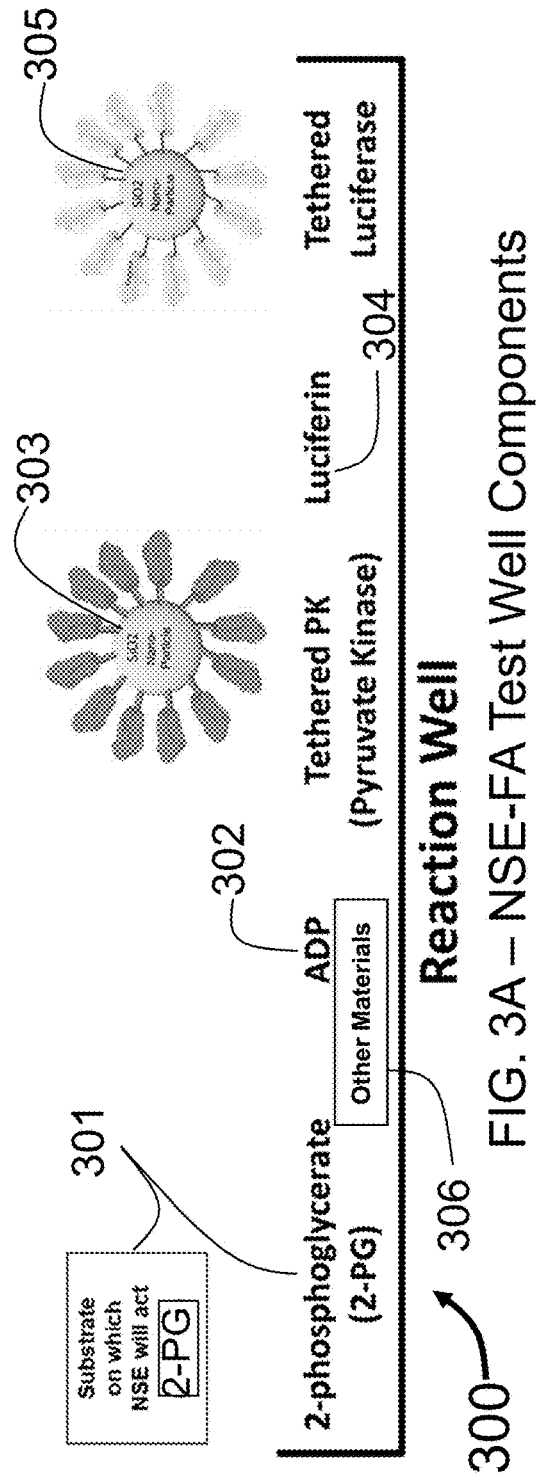
FIG. 3A – NSE-FA Test Well Components
FIG. 3B – NSE-FA Assay Process

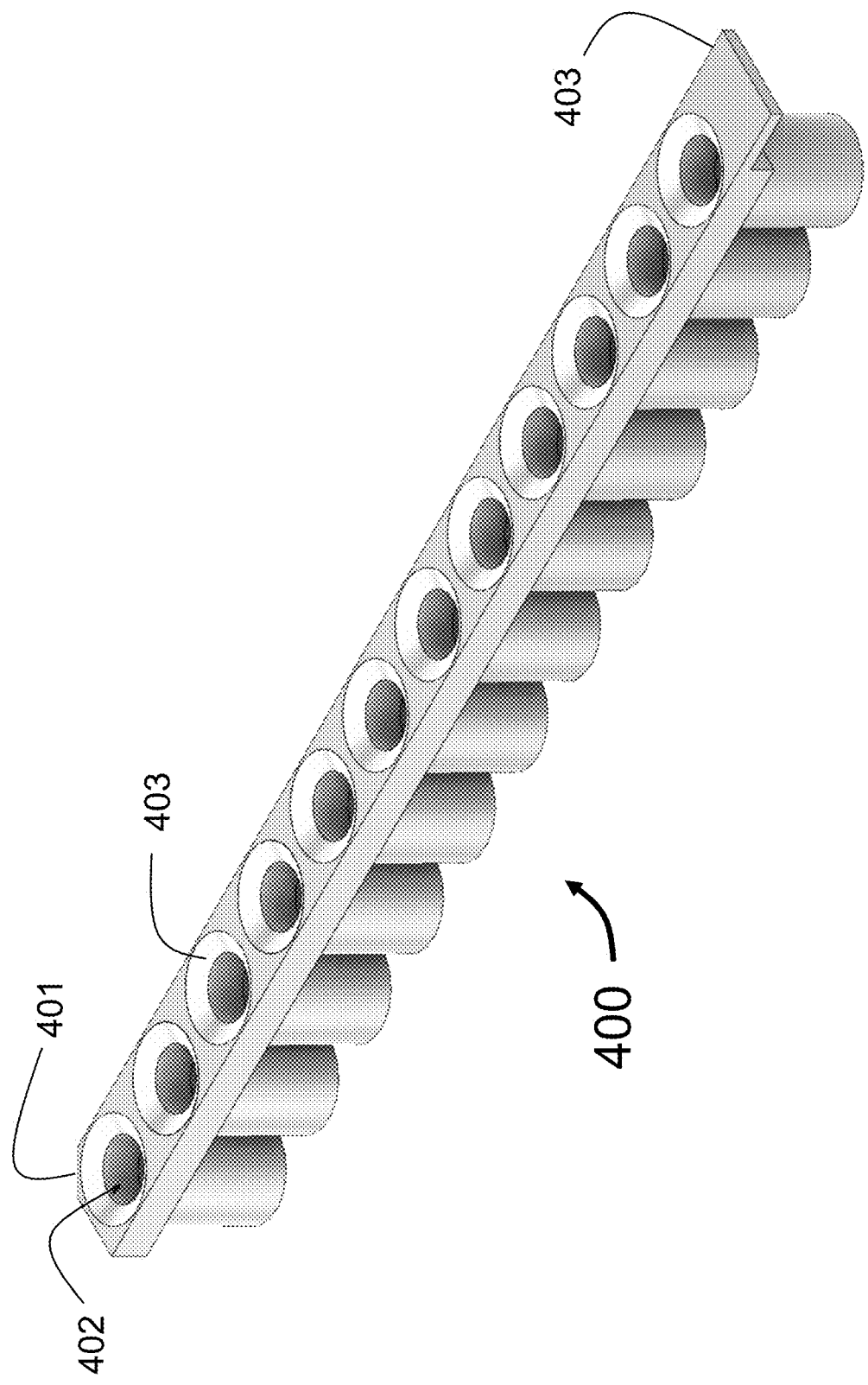
FIG. 4A – TET IVD Custom Assay Strip

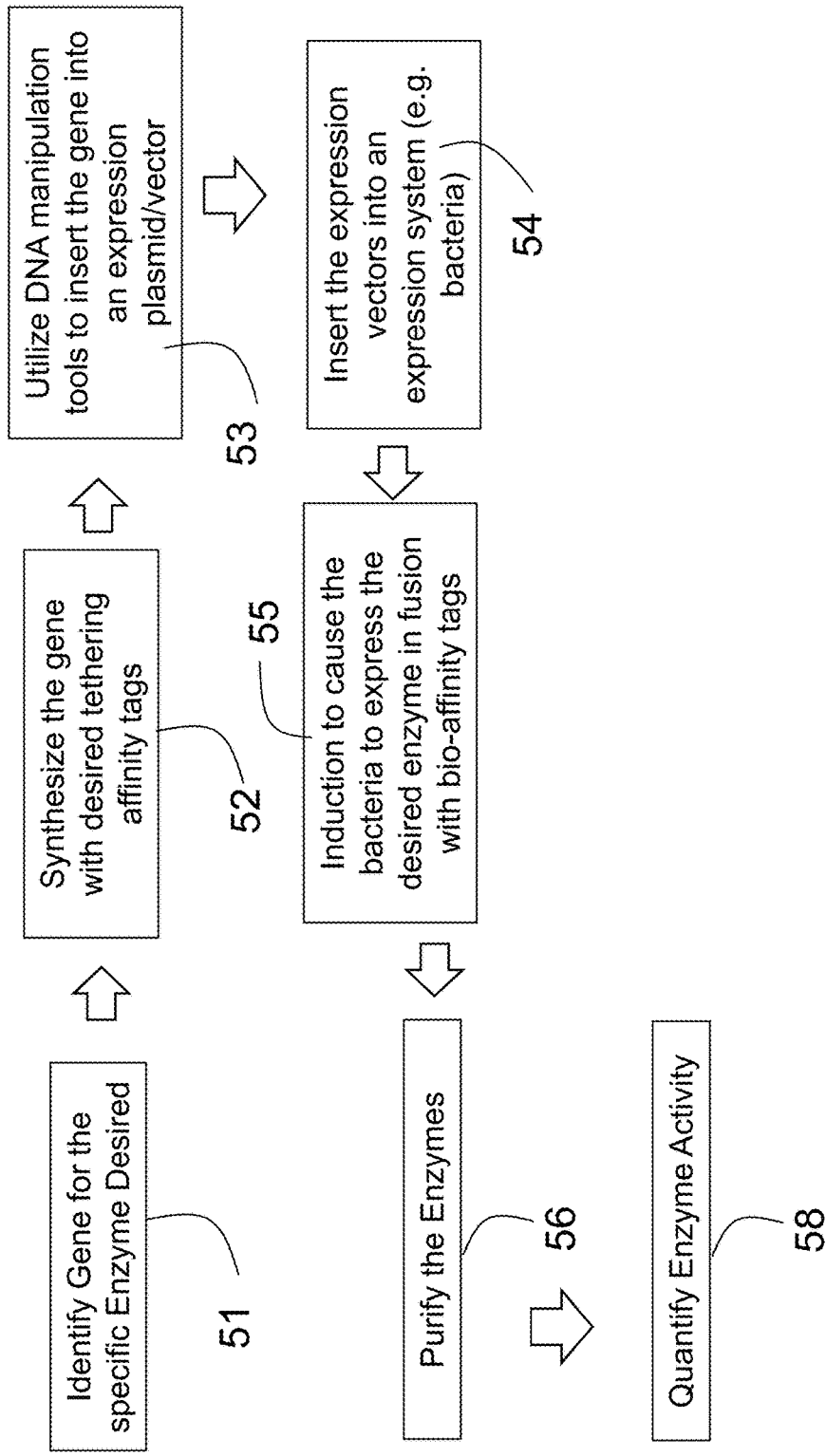
FIG. 5 – Enzyme Production Process

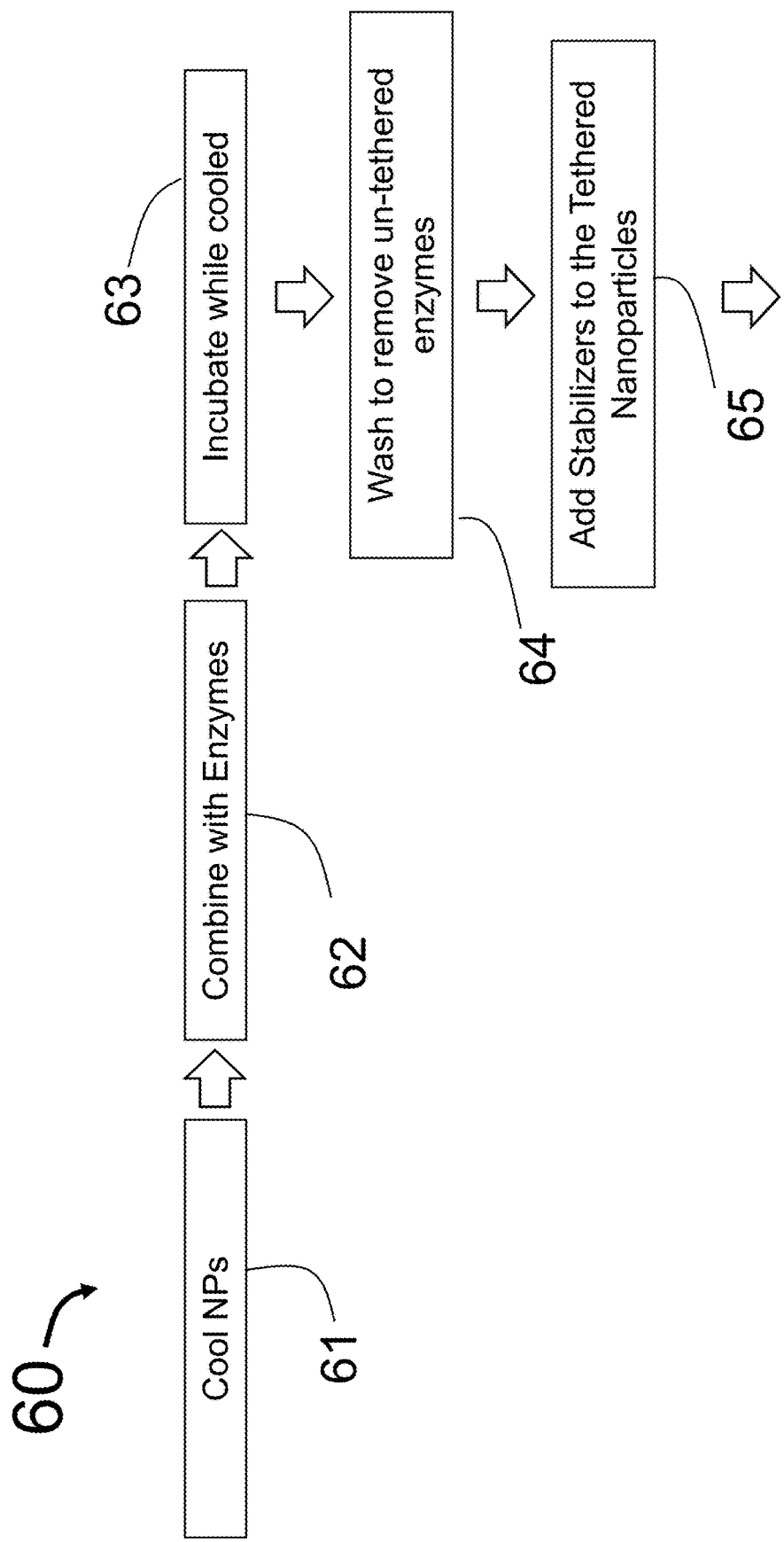
FIG. 6 – Enzyme Tethering Process

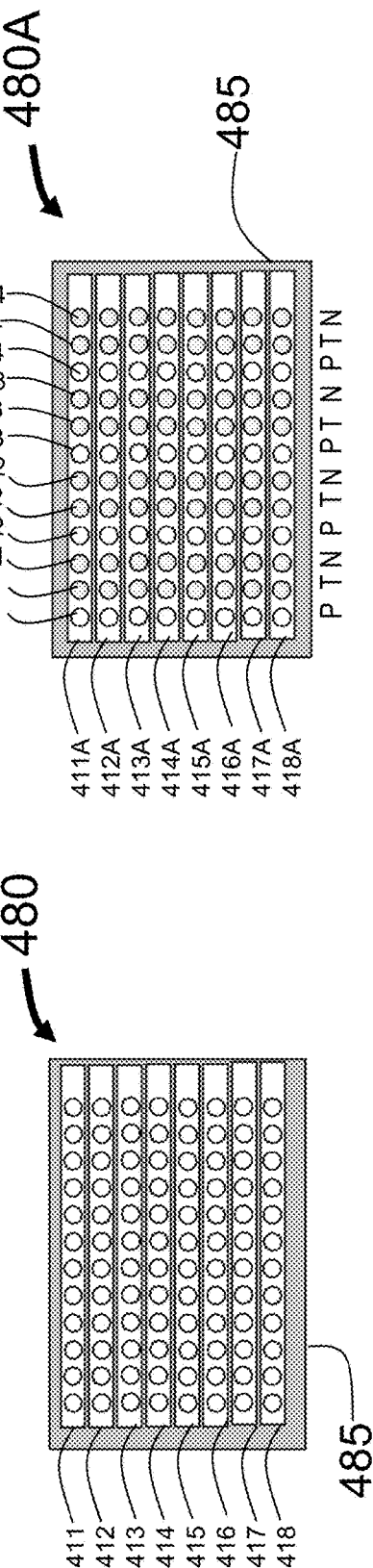
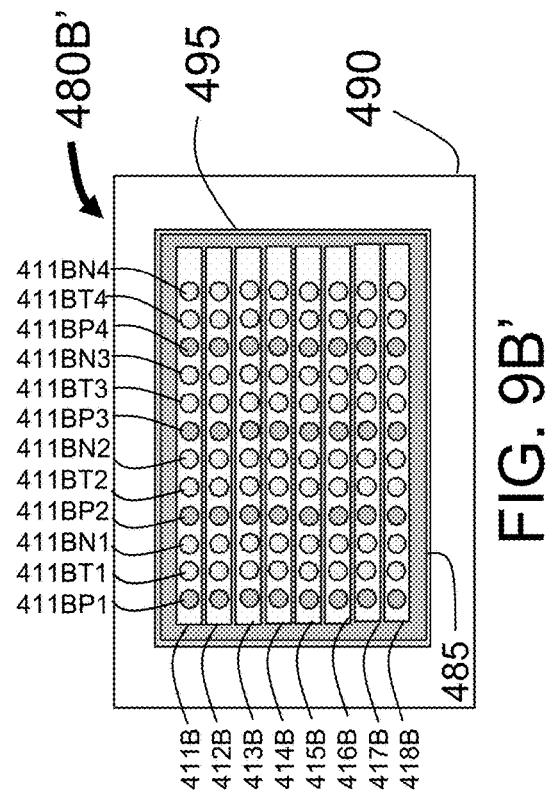
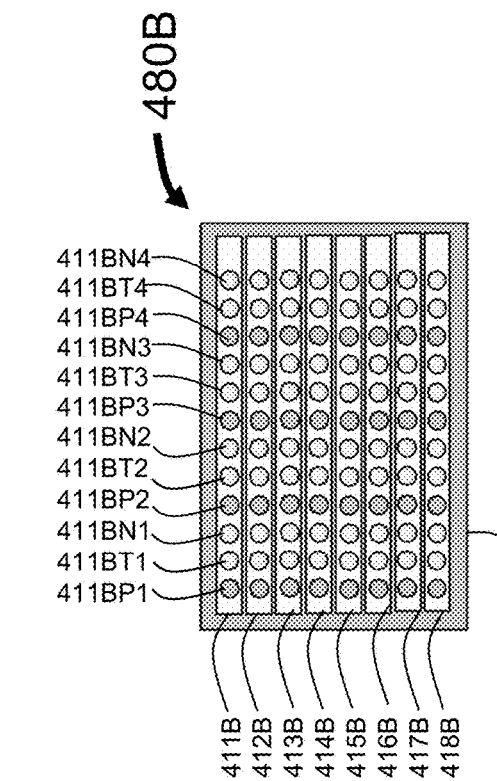
FIG. 9A
FIG. 9B'
FIG. 8
FIG. 9B

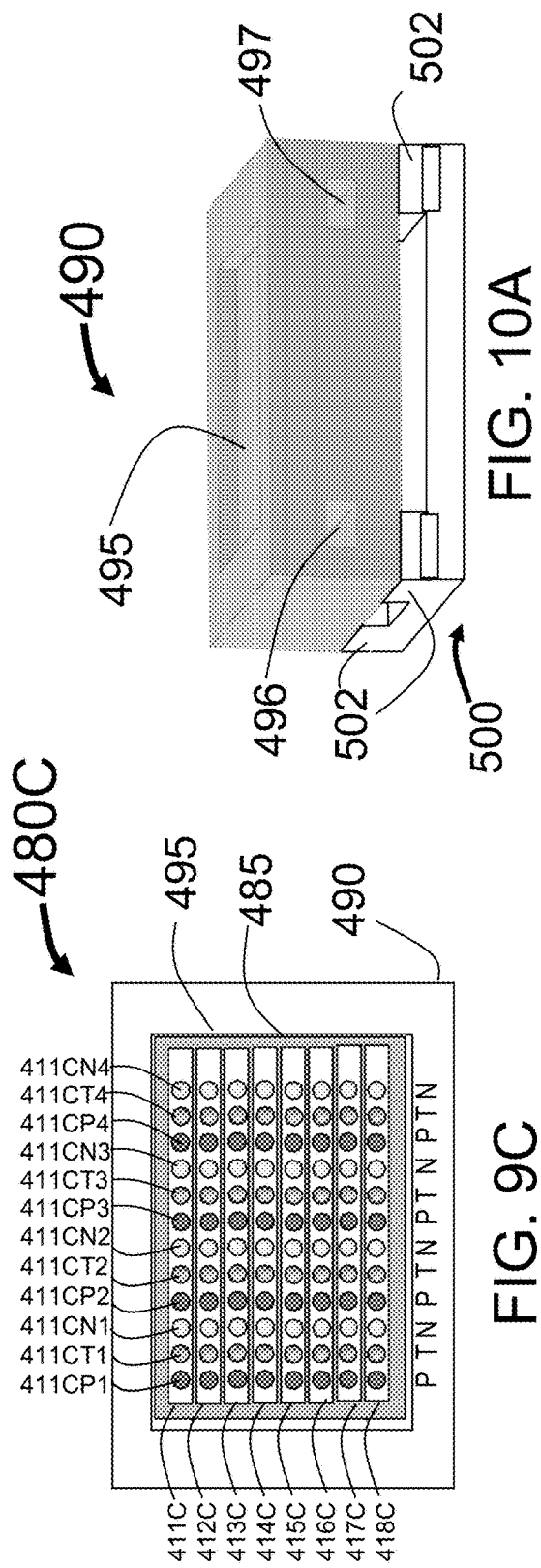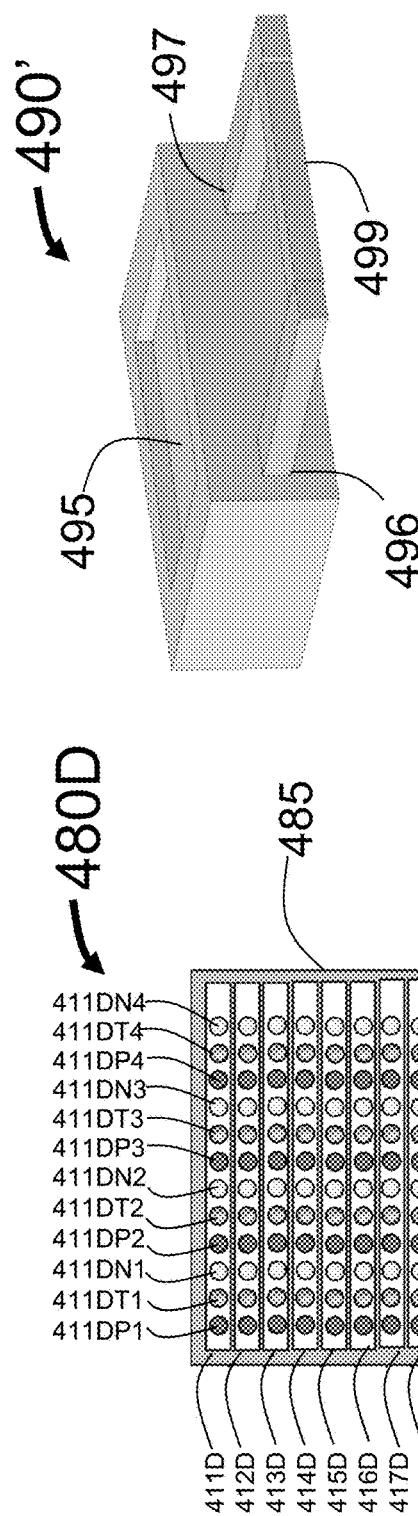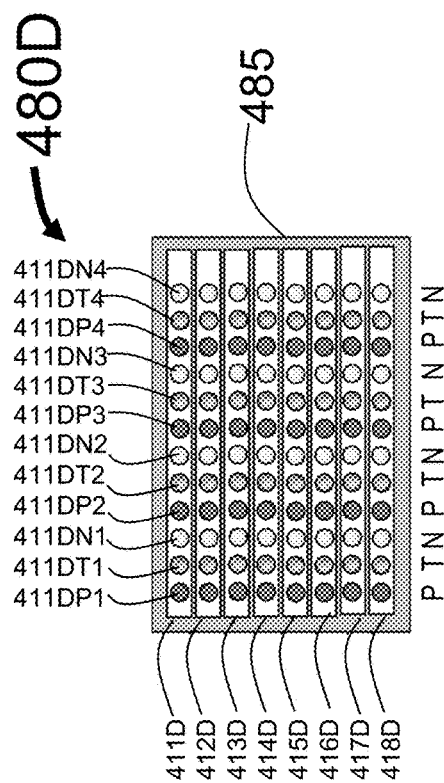

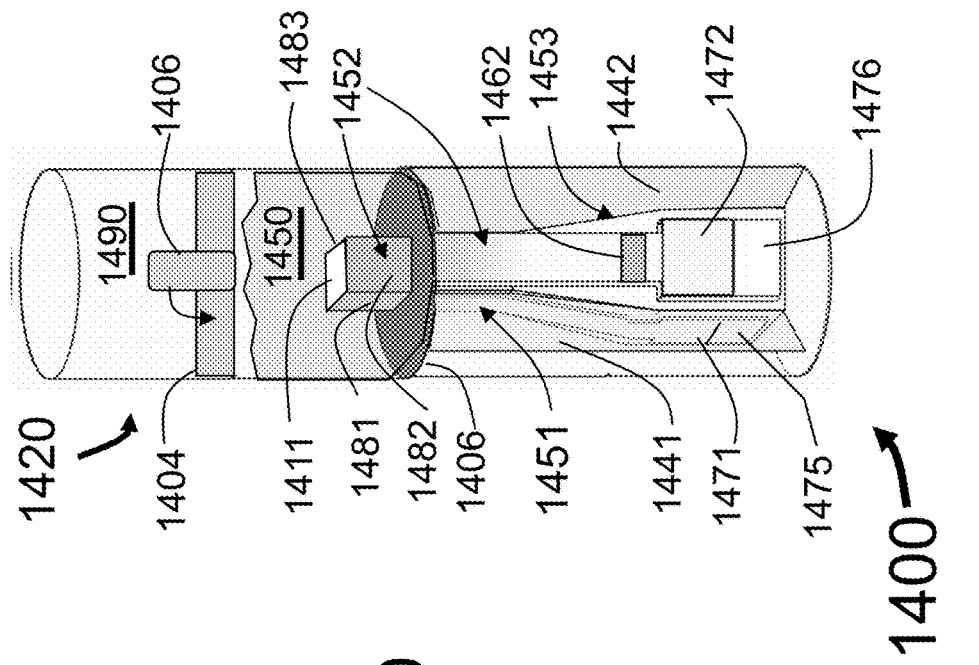
FIG. 14
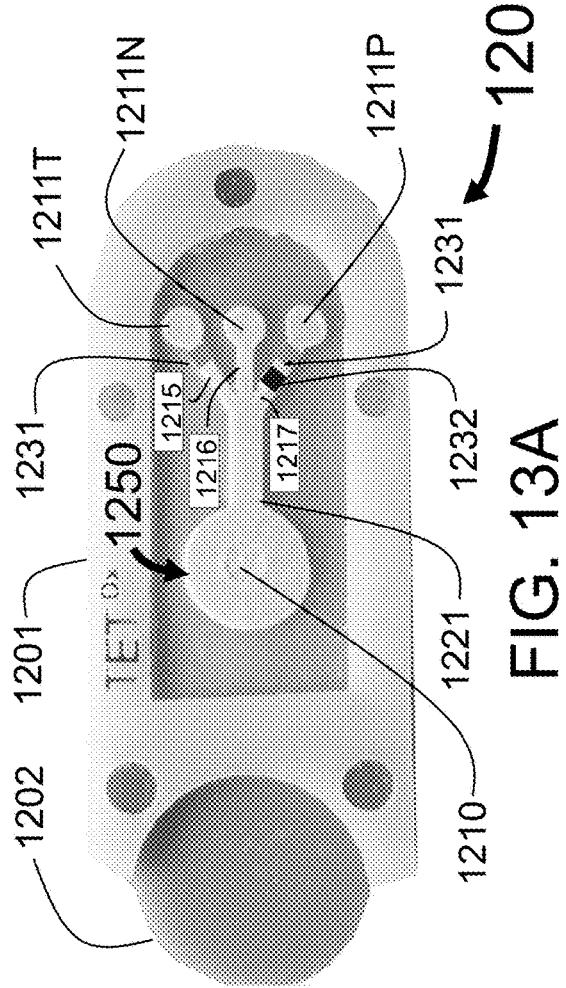
FIG. 13A
FIG. 13B

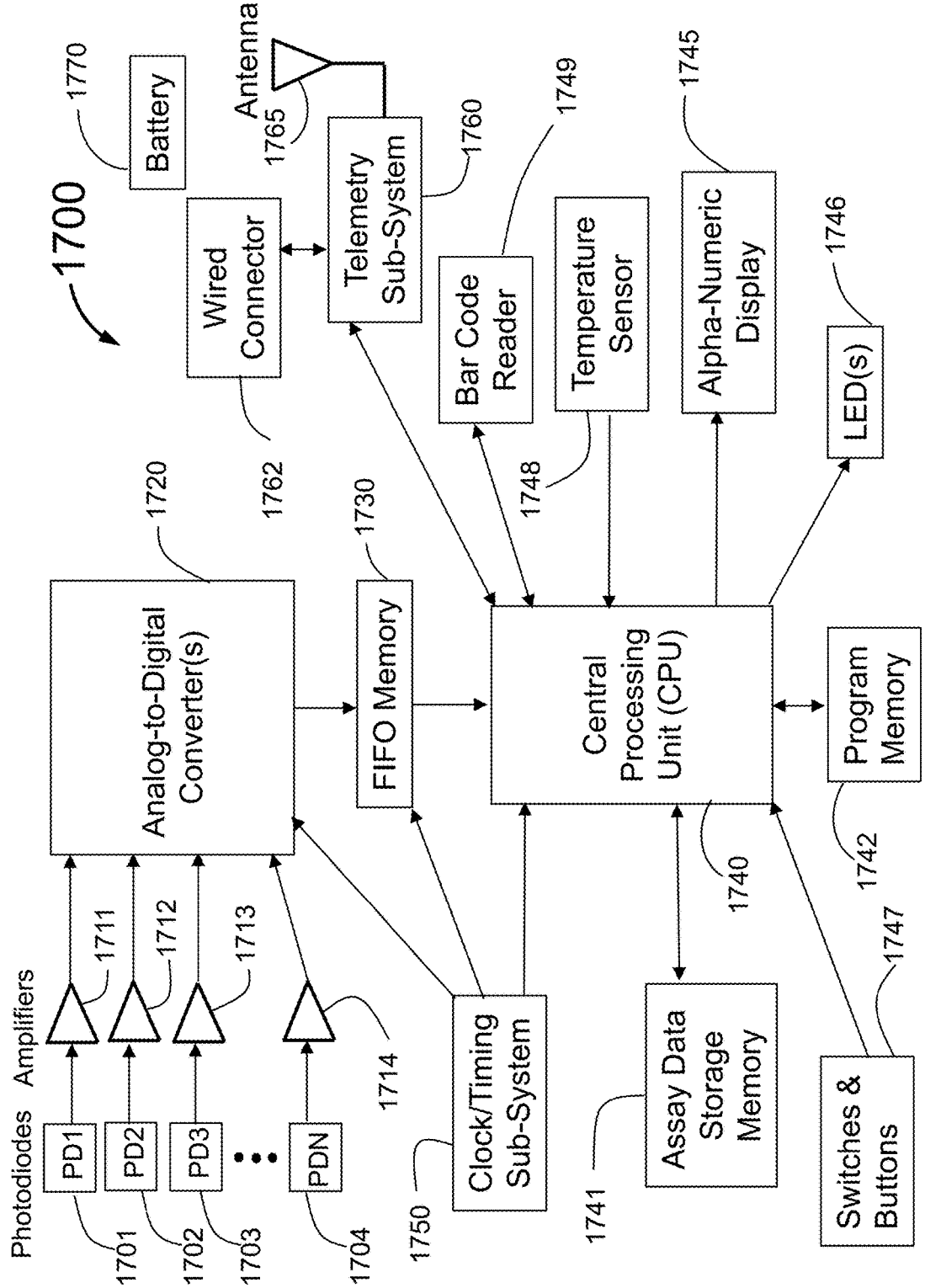
FIG. 17 – Microcomputer based PoC

APPARATUS AND METHODS USING TETHERED ENZYMES FOR THE DETECTION OF THE ENZYMATIC ACTIVITY OF BIOMARKERS

FIELD OF THE INVENTION

The present invention relates to tethered enzyme-based assays for the detection of biomarkers.

BACKGROUND OF THE INVENTION

There is a great clinical need for improved In-Vitro Diagnostics (IVD) and Point-of-Care ("PoC") Tests so that accurate diagnoses can be made quickly, enabling appropriate treatment or response as early as possible. A rapid detection system for the diagnosis of neural injury (e.g., stroke, concussion, trauma, aneurism) is especially important, because the treatment options for certain neural injuries such as stroke are extremely time sensitive, with maximal benefits occurring only if treatment can be initiated within the first few hours post-event. In addition, objective/quantitative diagnosis of patients presenting with suspected acute stroke upon arrival at a medical facility is largely limited to computerized axial tomography (i.e., CAT or CT scan), which can typically only accurately identify hemorrhagic strokes (i.e., bleeding in the brain). Such strokes constitute about 15% of strokes. The diagnosis of Acute Ischemic Stroke (AIS) depends predominantly on clinical evaluation based primarily on patient symptoms and clinical signs (e.g., National Institutes of Health Stroke Scale (NIHSS)), and no remarkable findings on the CT scan. Magnetic resonance imaging (MRI), can provide enhanced information, but is not as widely available and usually cannot be performed in a timely fashion, leaving emergency medical providers without a timely means to identify AIS or non-hemorrhagic brain injury. Accurate diagnosis is important, because stroke mimics (non-stroke conditions having similar presentations) account for at least 15% of treatments with tissue plasminogen activator (tPA). These over-treated patients are then put at risk of hemorrhage, and appropriate diagnostic work-up is delayed for their actual condition. In addition, an average of 17% of strokes are missed, with up to 40% of strokes missed when vertigo and dizziness are the main presenting symptoms. Furthermore, diagnosis of concussion in the field for military applications, or in athletic settings such as on the field, courtside or rinkside for civilian use, also depends almost entirely on symptoms with no device that can objectively identify a concussion where symptoms are not clearly evident.

Continuing the example of stroke, current diagnostic methodology relies on neurological expertise and advanced medical imaging techniques (e.g., CT & MRI), which are not widely available, and are time consuming and expensive. Because of these limitations, only 10-15% of patients suffering from ischemic stroke receive treatment with tissue plasminogen activator (tPA) within the 4.5-hour effective window (Otite et al., "Ten-Year Trend in Age, Sex, and Racial Disparity in tPA (Alteplase) and Thrombectomy Use Following Stroke in the United States," Stroke 52:2562-2570 (2021)). Today High Sensitivity Troponin is the standard of care for Acute Coronary Syndromes (ACS) including heart attack. A negative high sensitivity troponin result provides an accurate means to rule out ACS. Unfortunately, there is no current "Troponin for the brain" that can do for stroke what Troponin does for ACS and heart attack.

All together these issues create a large unmet need for a fast, accurate, highly-sensitive IVD for acute ischemic stroke to provide critical information on brain injury. Such a test would be of particular importance when the CT scan is negative for hemorrhagic stroke. As blood is already drawn for acute testing of patients presenting with stroke systems, this test, if fast enough, would not disrupt the workflow for the current Standard Of Care (SOC).

Currently, there are no widely available diagnostics that meet these unmet needs. Several new diagnostic technologies have been proposed including sonography, volumetric impedance phase-shift spectroscopy, and microwave tomography. Various biomarkers have been studied, with most detection approaches utilizing antibody-based capture of biomarker antigens, such as ELISA (Dewey H M and Howells D W (2021) Acute Stroke Biomarkers: Are We There Yet? Front. Neurol. 12:619721. doi: 10.3389/fneur.2021.619721 Dewey H M and Howells D W (2021) Acute Stroke Biomarkers: Are We There Yet? Front. Neurol. 12:619721. doi: 10.3389/fneur.2021.619721). One biomarker that has been studied for decades is neuron-specific enolase (NSE), but "although there appear to be multiple associations of NSE levels with stroke, at this time it does not appear that there is a defined role for serum levels of NSE in the diagnosis or prognosis of acute stroke patients" (Anand and Stead, Cerebrovasc. Dis., 2005, 20:213-219). In part, this is because of problems inherent with antibody-based diagnostic approaches, including variation among antibody affinities, inability of antibodies to differentiate between enzymatically functionally active NSE-FA that is acutely released versus inactive protein NSE-P that is steadily present in the peripheral circulation, and signal: noise challenges that arise from amplification of non-specific binding as well as specific binding. There are commercially available enzyme-based assays for enolase (e.g., Sigma, catalog Number MAK178) that could be used to detect activity via absorbance or fluorescence readouts; however, these are only available for research use and are not practical for direct measurement of NSE activity in fresh blood or blood products. These assays pose numerous barriers to clinical use in general, and particularly with regard to time-sensitive applications, such as the numbers of steps, storage conditions, shelf-life, and need to reconstitute multiple discrete reagents, the technical skills needed to perform these steps, lack of broad dynamic range, lack of standardization, lack of clinical interpretation for a given findings, etc.

Travis and Cohen in U.S. Pat. Nos. 9,547,014, 10,550,415 and 11,549953 that are incorporated herein by reference and U.S. patent application 63/005,785 2020/019924, and Ser. No. 16/729,793 (TET Prior Art) describe the techniques by which functional enzymes may be tethered to nanoparticles and other structures allowing increased stability for use in diagnostic and therapeutic applications. Specifically in FIG. 6A-6B of 9,547,014 (the NSE prior art assay), Travis and Cohen describe the assay to detect functional Neuron Specific Enolase (NSE-FA), an enzyme participating in the glycolysis pathway in neurons. NSE-FA in blood is increased as a result of injury to neurons in the brain. As the NSE was a functional, active enzyme (NSE-FA) before its release, it remains active for a number of hours before degradation to an inactive protein (NSE-P) where it loses its ability to function as an active enzyme. This permits use of the assay shown in FIG. 6A-6B of U.S. Pat. No. 9,547,014 to be able to be used to identify recent (acute) neuronal injury. It should also be noted that the prior art does not provide a description on how to produce a diagnostic assay with long shelf life for NSE-FA or for other enzyme biomarkers, nor does it describe a PoC test embodiment of the NSE-FA assay. The prior art discusses the use of positive and negative controls but does not identify the composition or techniques for producing such controls nor methods for their use in providing a qualitative and/or quantitative measurement of NSE-FA or other enzyme biomarker activity.

The TET Prior Art also mentions tethering of enzymes using oriented immobilization to be used in the detection of biomarkers but does not describe the process by which it is accomplished. Such oriented immobilization provides advantages in stability to increase shelf life as well as increased sensitivity in coupled enzyme reactions where a sequence of tethered enzymes work sequentially to produce a measurable signal as described in the TET Prior Art.

Because of the enormity of the clinical need, much attention is focused on developing PoC/at home diagnostic tests to detect pathology-specific biomarkers. Biomarkers for such tests include proteins, lipids, sugars, nucleic acids, or ions. Blood biomarkers for neural injury have received much attention due to the difficulties regarding timely clinical diagnosis. Currently, over 50 candidate bio-molecules including proteins, metabolites and nucleic acids have been identified and investigated for varied applications in diagnosis, outcome prediction, or treatment of stroke (Jickling and Sharp, "Blood Biomarkers of Ischemic Stroke," Neurotherapeutics 8(3):349-60 (2011); Saenger and Christenson, "Stroke Biomarkers: Progress and Challenges for Diagnosis, Prognosis, Differentiation, and Treatment," Clin. Chem. 56(1):21-33 (2010); Whiteley et al., "Blood Markers for the Prognosis of Ischemic Stroke: A Systematic Review," Stroke 40(5): e380-9 (2009); Hasan et al., "Towards the Identification of Blood Biomarkers for Acute Stroke in Humans: A Comprehensive Systematic Review," Br. J. Clin. Pharmacol. (2012); Glushakova et al., "Biomarkers for acute diagnosis and management of stroke in neurointensive care units," Brain Circulation, 2:28-47 (2016); Kamtchum-Tatuene and Jickling, "Blood Biomarkers for Stroke Diagnosis and Management," Neuromolecular Med. 21(4):344-368 (2019); and Bejleri et al., "Diagnostic and Prognostic Circulating MicroRNA in Acute Stroke: A Systematic and Bioinformatic Analysis of Current Evidence," 23(2): 162-182 (2021)). The growing list of potential biomarkers provides a useful resource to guide the development of PoC diagnostic technologies. However, there remains a great need for a rapid, easy-to-use, highly-specific detection system for the diagnosis of neural injury, that has a low Limit of Detection (LOD) for the target analyte, which itself is preferably highly-sensitive for detection of the condition of interest (e.g., stroke).

Several examples of PoC biomarker detection technologies for the diagnosis of various diseases have recently been described. These technologies are divided into 3 major categories including chemical-, immunoassay- or nucleic acid-based detection systems with various signal readout methods such as absorbance, fluorescence, luminescence, electrochemical and colorimetric methods (Chin et al., "Commercialization of Microfluidic Point-of-Care Diagnostic Devices," Lab Chip (2012)). This list includes Atolyzer® (Atonomics), Triage® (Alere), Spinit® (Biosurfit), and i-STAT® (i-STAT Corp). However, despite such PoC systems, there remains a great need for increased sensitivity and speed in detecting biomarkers, especially neural injury biomarkers and assays for liver and kidney function. With the potential for liver and kidney damage, patients undergoing chemotherapy or other drug regimens have need for frequent blood tests. This requires travel to a test lab today, which poses logistical barriers such as means and accessibility of transportation, missed employment, etc., as well as inconvenience. New at-home blood sampling devices like the TASSO (Seattle, WA) will allow blood samples to be taken and mailed to a test lab. This too has its pitfalls as such mailing and handling of biologics can degrade the sample and mailing is subject to delays, potentially delaying results for days. Today the only at home blood tests available are for glucose for blood sugar monitoring (e.g., for diabetics). While at home/PoC tests for more complex biomarkers like SARS-CoV-2 proteins and/or antibodies are now available, such tests are limited to saliva.

Beyond neural injury, there are a great many applications also in need for PoC diagnostics. For example, bacteria transferred primarily from the mother can cause significant unsolved dental problems in children resulting in the need for expensive sealant treatments to prevent chronic tooth decay. These bacteria produce a surface expressed enolase enzyme (among others) that if detected in either mother or child could be used to identify early need for appropriate treatment.

PoC tests that can be used at home or in a doctor's office for monitoring liver and kidney function do not exist and are also needed both for patients suffering from chronic diseases as well as the monitoring of numerous therapies including drug regimens and chemotherapies. Furthermore, ability to test for liver and kidney damage and/or function at home could also accelerate and improve the safety of drug testing, reducing burdens on trial participants and costs, while increasing the demographic and geographic diversity of participants. An at-home blood test that could utilize a device like a TASSO to draw the sample and provide data that can be transmitted electronically to the patient's doctor would have huge benefit. Achieving luminescence based enzymatic assays for measurement of liver injury markers ALT and AST directly from fresh blood products has been challenging. Specifically, advanced enzyme-based technologies that utilize hydrogen peroxide ($H_2O_2$) production to generate luminescence or fluorescence readout have only demonstrated functionality in buffer solutions References include:

Ecem Saygili, Beyza Orakci, Melisa Koprulu, Alper Demirhan, Esra Ilhan-Ayisigi, Yalin Kilic, Ozlem Yesil-Celiktas, Quantitative determination of $H_2O_2$ for detection of alanine aminotransferase using thin film electrodes, Analytical Biochemistry, Volume 591, 2020, 113538, ISSN 0003-2697

Thuy, T. N. T.; Tseng, T. T.-C. A Micro-Platinum Wire Biosensor for Fast and Selective Detection of Alanine Aminotransferase. Sensors 2016, 16, 767. https://doi.org/10.3390/s16060767

Hsueh C J, Wang J H, Dai L, Liu C C. Determination of alanine aminotransferase with an electrochemical nano ir-C biosensor for the screening of liver diseases. Biosensors (Basel). 2011 Jul. 12; 1(3):107-17. doi: 10.3390/bios1030107. PMID: 25586923; PMCID: PMC4264364

There is thus a strong need for a PoC device similar to the Lucira™ Covid test now sold by Pfizer that can work with a sample of blood, plasma or serum from a blood collection device like the TASSO® device that can provide at home, ambulance or doctors offices results from a luminescence assay.

For the purposes of this specification, the term "biomarkers" is meant to be inclusive of all analytes, including complex organic compounds, enzymes, simple elements and compounds, DNA, RNA, and any other organism, organic, or inorganic structure that provides important information on patient or environmental condition.

The present invention is directed to overcoming these and other deficiencies in the art, inclusive of applications in human and veterinary medicine, and environmental diagnostics.

SUMMARY OF THE INVENTION

The present invention is a tethered enzyme platform, system and method for assays to detect important medical biomarkers and analytes using Tethered Enzyme Technology (TET). TET represents a significant advance in medical diagnostics compared to prior art in the form of antibody based In-Vitro Diagnostics (IVD). This platform can also be applied to molecular diagnostics such as polymerase chain reaction (PCR) or reverse transcription-PCR (RT-PCR). The advances include:

Simplicity with minimal user effort—simply pipette serum, plasma or other liquid samples containing the biomarker into the wells.

Less effort—due to high sensitivity and specificity there is a significant reduction in needed reaction wells. Only 1-4 sample reaction wells and a similarly small number of positive and negative control wells are needed for a specific biomarker compared to 20 or more wells often needed for antibody-based assays.

Speed—due to the catalytic nature of enzymes, results are produced in as little as 30 seconds.

Customization—with the ability to detect a wide range of biomarkers including enzymes, enzyme substrates, metabolites, ions, and nucleic acid sequences such as DNA (deoxyribonucleic acids), RNA (ribonucleic acids) and microRNA (non-coding short sequences of RNA), in separate or multiplexed assays with a common readout.

Assay stability—tethered enzyme reagents are highly stable compared to enzymes in solution. Lyophilized (freeze-dried) TET reagents have been found to be stable for over a year.

Point-of-care applications—realizable using simple blood filtration papers and the combination of sensitivity, specificity, speed, stability and simplicity.

Unique—The TET Funtional Activity Stroke Test (NSE-FAST) NSE-FA assay would be the first-in-class objective measurement for acute brain injury associated with stroke and its PoC version being the only PoC assay for acute brain injury.

Utility—TET assays can be used to detect diverse analytes and biomarkers including enzymes (e.g., ALT and AST), and metabolites, ions and other small molecules (e.g., potassium, magnesium, calcium, iron ions, Nicotinamide adenine dinucleotide (NAD), NADH is the reduced form, Nicotinamide adenine dinucleotide phosphate (NADP) and its reduced form (NADPH) creatinine and uric acid), to monitor liver and kidney function respectively. A PoC device could be used for patients suffering from chronic diseases as well as the monitoring of response to numerous therapies including drug regimens and chemotherapies.

The present invention includes novel embodiments of nanoparticle-tethered enzymes (TET nanobots) that provide a significant increase in coupled enzyme activity and stability compared to untethered enzymes and enzymes tethered via non-specific or chemically-specific but biologically non-oriented immobilization techniques. In embodiments of the present invention, TET nanobots improve substrate access to the enzyme's active site, and conformational freedom needed for the enzyme to be functionally active. The combination of one or more TET nanobot building-blocks into a single assay reaction enables the detection of different analytes.

In addition, tethering of more than one enzyme in a detection system utilizing a coupled enzyme reaction pathway, produces substantial benefits in the specific activity of the coupled reactions versus when enzymes are in solution or attached to a surface via a non-oriented approach (e.g., Cohen 2015, Mukai, 2013, Mukai, 2017)

For the remainder of this specification, the terms "well" or "zone" may both be used to describe any volume where a TET related assay reaction occurs. These include but are not limited to a well in an IVD assay multi-well strip or plate, or a zone on a filter paper, sheet material, or other volume in a PoC or IVD assay device.

The present invention TET assay embodiments provide a significant advance in speed due to the catalytic nature of enzyme function (up to hundreds or thousands of reaction events per enzyme per second), the channeling or proximal diffusion of coupled reaction intermediate products from one tethered enzyme to the next ("substrate channeling"), and the ability to provide oriented immobilization of a thousand or more enzymes on each individual nanoparticle. Thus with up to millions of reactions per second per nanoparticle and thousands of nanoparticles per reaction well, this amplification of the tethered enzymes in TET assays can provide a significant speed advantage over non-enzymatic biomarker detection (e.g., antibody-based) —and some other enzyme-based assays that do not use tethered enzymes with oriented immobilization. The reaction efficiency of conversion from substrate to product can also be improved, particularly for coupled enzyme reactions.

The novel embodiments described herein include specific TET assay elements that facilitate the catalytic chain reaction that provides the ability to detect biomarkers at rapid speeds (e.g., less than 5 minutes), from contact of the sample with the TET nanobots. This speed is of particular importance in both IVD and PoC assays for time-critical diagnosis of acute brain injury from stroke, concussion or difficult childbirth.

The present invention TET assay embodiments for both IVD and PoC are manufactured using a novel method that includes:

1. Production of the enzymes to be tethered by introduction of coding genetic material (e.g., DNA or RNA sequences) into a biological entity or system that will then produce the needed enzymes suitable for tethering. The biological entity may be mammalian cells, insect cells, yeast or bacteria. The system may also be a "cell-free expression system" containing elements typically found in one or more of the above entities or completely artificial (e.g., protein printing). One or more follow-on purification steps may be included.

2. Tethering of the one or more selected enzymes to nanoparticles to form the nanobots that produce the diagnostic tethered enzyme (chain) reaction in one or more test, positive control or negative control wells, and/or additional select controls such as for sample quality such as presence of hemolysis, and/or for additional biomarker specificity, such as for sub-types, isoforms, or other variants of a common base biomarker molecule. Note that for sake of simplicity, we use wells as an example, but wherever used, "wells" should be thought to represent various physical devices with various material compositions, including but not limited to paper strips, paper pads, microfluidic channels, other chambers, surfaces, etc., upon or into which the nanobots can be placed or localized.
3. Use of a multiple step freeze/freeze-drying/drying process and layered introduction of materials into test, positive control, negative control, and/or other control wells or zones. This process prevents untimely/premature activation of the diagnostic wells most important for positive controls, better mixing of the TET reagents with the bio-fluid/sample, and provides for a long shelf life. This process also provides for efficiency in laying down materials in the wells to create the test, negative control, positive control and other control wells. Fast mixing is important to provide rapid separation of the luminescence curves from test, negative and positive control wells.
4. Use of a custom IVD strip or a custom PoC structure designed to maximize the efficiency of capture of the output signal (e.g., luminescence) from the wells, improve user convenience and optimize sample addition. Microwell embodiments could range from single wells, to small numbers of wells, to strips of wells of varying length, all of which could be manufactured to fit within a holder or adaptor, enabling usage in standard plate readers.
5. Use of an automated dispensing system to accurately pipette the well mixtures in layers into the wells for production and/or device quality testing.
6. Use of specific paper filtration, microfluidics, or other separation mechanisms for the PoC assay, in which blood plasma is separated from blood cells and cell fragments, and in which the plasma will reach the reaction zones/wells in a timely manner with sufficient concentrations to trigger the TET coupled enzyme reactions.
7. Use of a TET PoC device that includes a detector technology (e.g., photodiodes for detection of luminescence output), and a microcomputer to perform a novel algorithm based on the signal output results of test wells and controls to provide both quantitative and qualitative measurements of biomarker presence.
8. A pre-treatment of blood or plasma samples to allow direct measurement of liver enzymes or other analytes that cannot be detected in plasma using luminescence or other desired readouts.

Embodiments of the present invention IVD and PoC use three (or more) types of wells and include a calculation or algorithm for measurement and threshold-based evaluation of biomarker level. For the NSE-FAST this can provide the first objective diagnostic for significant acute brain injury from stroke.

With the future of medicine moving more and more toward telemedicine and the need to provide remote assessment of patient condition, the ability of the present invention TET assays to provide point-of-care (PoC) diagnosis in the ambulance, doctor's office, in the home and at the athletic playing venue will become more and more important. For the purposes of this specification, PoC diagnosis includes use of a diagnostic device or assay without the use of the equipment typically found in central diagnostic laboratories (e.g, Labcorp, Quest, or Eurofins) or in a hospital based diagnostic laboratory.

The TET prior art describes use of a multiple stage coupled enzyme reaction with the final stage providing a signal indicative of the assay measurement. These signals include color change, electrical outputs and fluorescence/luminescence. The present invention IVD and PoC embodiments may use any of those signals; however, a preferred embodiment would be the use of luminescence as the significant number of photons produced can be easily measured in embodiments using standard photosensitive assay readers for IVD and inexpensive photodiodes for PoC implementations. Three other important advantages of luminescence include high dynamic range, linearity of the readout, and low background signal.

In an embodiment, a TET IVD Diagnostic Assay System (TET-IVD) would utilize an assay strip with multiple wells that is insertable into a standard assay plate reader. A liquid sample containing the biomarker would be pipetted into each well; the strip is then inserted into a plate reader or plate reader-like device where a custom algorithm or set of calculation/algorithms would compare the luminescence, fluorescence, absorbance or color change from the test, negative control and positive control wells to measure the biomarker presence and amount/activity in the sample.

In another embodiment, a TET Point-of-Care Device (TET-PoC) would include electronics attached to photodiodes for the detection of light produced in the test and control wells by an assay, for example, the assay of FIG. 6A-6B of U.S. Pat. No. 9,547,014 where a TET particle utilizes an enzyme that will luminesce such as Luciferase or HRP (Horse Radish Peroxidase).

Another embodiment could use a luminescent protein or chemical reactions that are coupled to upstream enzymes. For example one can use myoglobin (which is not an enzyme) to generate light when in contact with luminol in the presence of $H_2O_2$ produced by an upstream oxidase enzyme.

In an embodiment the TET-PoC has two separable parts, a blood or bio-fluid handling part and an electronic part. The electronic part may be disposable or reusable with the fluid handling part being single use and disposable. It is envisioned that a blood microsampling device such as the TASSO® device made by TASSO®, Inc. could be used to quickly collect a sufficient size blood sample for the TET-PoC.

In a preferred embodiment, the TET-PoC is a disposable unit with both electronics and fluid handling pieces integrated into a single device. For example if the TASSO microsampling device is integrated with a blood filtering mechanism, then plasma can flow into the reaction zones of the TET-PoC where the luminescence can be measured by included photodiodes.

In the preferred embodiment, the TET-PoC is battery powered with electronic circuitry. In other embodiments, the battery powered TET-PoC includes one or more of the following features:

Photodiodes to monitor the test, positive, negative, and other control wells,

A timer mechanism that disables the device after a pre-set number of days or weeks to ensure the device is used only before its expiration date, Means to activate the start of the timer mechanism. This can be an actuator, for example, a button, switch or a temperature sensor that activates when the TET-PoC reaches a specified temperature, An algorithm implemented in circuitry, a microcomputer or microprocessor to perform calculations for quantifying a biomarker from the measured luminescence of the zones/wells, An algorithm implemented in circuitry, a microcomputer or microprocessor based on the luminescence produced by the reactions in the zones/wells to make a threshold-based, yes/no decision, An algorithm implemented in circuitry, a microcomputer or microprocessor to perform calculations to identify error conditions, One or more numerical displays, for example a numerical display labeled "AST" and a second numerical display labeled "ALT" both on the TET-PoC to provide liver enzyme data, One or more visual indicators, e.g. LEDs, that provide a yes/no; low, medium, or high; error or other indication of the assay result or TET-PoC status, Wireless networking of the TET-PoC to local and/or remote smart devices to deliver the test results, Use of paper filter micro-channels for wicking blood and/or blood plasma in the TET-PoC from a blood source to the zones/wells containing tethered enzymes and other components for detecting one or more biomarkers. The micro-channels would be 1-10 mm in diameter and in embodiments would include one or more elements selected from the group including:
1. reservoir paper that wicks whole blood,
2. a filter mechanism e.g., filter paper that restricts movement of blood cells and cell fragments, but allows plasma to flow on, and
3. zones/wells comprising one or more assay components including one or more tethered enzymes for detecting a biomarker.

In an embodiment, the TET assay (IVD or PoC) has a multiplicity of test wells/zones including at least one assay test well and at least one negative control well. For example, in a preferred embodiment for the detection of NSE functional activity (NSE-FA), the formulation in the at least one negative control well includes all the components in the test well for detecting NSE except 2-phosphoglycerate (2-PG).

In an preferred embodiment, the TET assay has a multiplicity of test wells/zones including at least one assay test well/zone, at least one negative control well/zone and at least one positive control well/zone. The test, negative control and positive control wells are freeze dried and only become active when they become wet from the presence of the liquid including the potential biomarker, e.g., plasma or serum.

It is also envisioned that an embodiment of the present invention TET-IVD or TET-PoC could have only one zone for test reaction.

In a preferred embodiment for the detection of NSE-FA, the formulation of the positive control well(s)/zone(s) includes one or more of the following components to produce a positive reaction when the Tethered Enzyme-based ingredients are activated:
1. 2-PG+Enolase
2. Phosphoenolpyruvate (PEP)
3. Adenosine Triphosphate (ATP)

In a preferred embodiment using Enolase in the positive control well(s)/zone(s), the Enolase is tethered to nanoparticles to improve stability and shelf life.

In an embodiment additional wells/zones may be used in the TET IVD or PoC assays to adjust the final measurement of the biomarker. For example, the TET NSE-FA assay as described by Travis and Cohen in U.S. Pat. No. 9,547,014 may be sensitive to enolase sources from non-neuronal sources that have a different characteristic than NSE-FA. Use of an inhibitor of NSE-FA in an additional well that can be compared to the test well, or use of an inhibitor of non-neuronal enolase in the primary test well, or use of an inhibitor of non-neuronal enolase in an additional well that is used to identify the amount of non-neuronal enolase by comparison, can be used in the NSE-FA assay measurement. This can be of most advantage to eliminate measured non-neuronal enolase (e.g. from hemolysis) that could affect the measured assay output. It is also envisioned that use of a color chart to reject plasma or serum with too much hemolysis may be utilized to reject samples.

It is envisioned that to provide an internal test for within-sample reproducibility, 2 or more wells of each type could be used. In a preferred embodiment there is at least one positive control well, at least one negative control well and at least two assay test wells. In a preferred embodiment that minimizes the amount of sample fluid needed for the assay, there is one positive control well, one negative control well and one assay test well. Other embodiments and algorithms to provide consistency are also envisioned such as having 4 of each type of well/zone where the high and low are rejected and the middle two are averaged. Another method would reject any well/zone that is an outlier with the others averaged together. These calculations may apply to the direct luminescence values or to the luminescence curve slopes.

In an embodiment, the IVD or PoC assay includes an algorithm with one or more calculations that can identify significant acute neural injury by comparing the measured luminescence from the test wells with the luminescence from the negative control well and/or the positive control well.

In a preferred embodiment the measurement includes the determination of the slopes of the luminescence outputs of test, positive control and negative control wells.

In an embodiment the amount of 2-PG in test wells for NSE-FA is provided in enough quantity that it is not limiting to the reaction such that the limiting component of the reaction is the amount of NSE-FA.

Because a positive control well using the formulation of item 1 above (2-PG and Enolase) will produce a signal that not only depends on the activity of Enolase in the positive control well but the amount of NSE-FA or other Enolase activity introduced in the sample, the activity generated by the positive control alone can be obtained by subtracting from the luminescence of the positive control well, the value of the luminescence from the test well that includes the background luminescence as measured from the negative control well as well as the luminescence generated by NSE in the sample.

In an embodiment, the approximate luminescence generated by the NSE in the sample in the test well can be obtained by the subtracting out the luminescence from the negative control well.

In embodiments, it is envisioned that additional mathematical manipulations can be performed to adjust for non-linearity of readouts from one or more wells.

In an embodiment a threshold for detection of an amount of NSE-FA that reflects a pathological state can be set as a percentage of the measured slope of the positive control well luminescence or the difference between the measured slopes of the luminescence of the positive and negative control wells.

In an embodiment a threshold for detection of an amount of NSE-FA that reflects a pathological state can be set as a percentage of the initial reaction slope of the true positive control well luminescence that already subtracts out the negative control well luminescence.

During blood draw, hemolysis may occur that could reduce the effectiveness of the test for NSE-FA. An embodiment of the present invention includes one or more additional wells with a TET-based assay specific to hemolysis that would provide information that can be used to differentiate brain injury from enolase present in blood cells and then released upon hemolysis.

In an embodiment, significant signal from the negative control well or lack of signal from the positive control well will initiate an error condition and subsequent display to the user of the TET-PoC. A similar reading may also result in error conditions for an IVD.

In an embodiment, the TET-PoC includes chemicals in the test well that produce color changes from an assay such as the assay of FIG. 6A-6B of U.S. Pat. No. 9,547,014. Such color changes could be similar to that seen in a COVID-19 antigen test, or pregnancy test.

An embodiment of the TET-PoC would also include a separator to limit movement of blood cells allowing only plasma or serum to flow into the assay wells/zones. This is important as the red blood cells can interfere with the measurement of luminescence. Examples of separators include membranes, filters, chromatography paper, microfluidics, mini centrifuges and magnetic bead separation systems such as those described by Vemulapati in European Patent Application EP3823761A1.

In another embodiment the present invention TET-PoC includes means to extract blood from a human body. For example—if combined with the TASSO® blood draw device of U.S. Pat. No. 10,426,390, the integrated TET-PoC could be used to provide a rapid diagnostic test within a few minutes without need for a phlebotomist, or to send the blood sample drawn by a phlebotomist or a device such as the TASSO device to a separate lab.

It is also envisioned that in a preferred embodiment, rather than combine the blood draw device and TET-PoC, a compatible vial that can be removed from the blood draw device would then be inserted into a TET-PoC reader to start the assay. This embodiment also has the advantage of being usable with any blood draw device or means for placing patient blood into a vial.

It is also envisioned that the present invention TET IVD assay may be designed to be inserted into a standard plate reader device. In an embodiment, a TET assay strip of 3 or more wells would be used with a preferred embodiment of 12 wells.

An embodiment of the TET assay may include multiple biomarker assays including separate test wells, negative control well or wells, positive control well or wells, and other control well or wells for each assay. In a preferred embodiment for certain assays, a negative or positive control well may serve for multiple biomarker assays.

Thus an object of the present invention is to provide an in-vitro diagnostic capable of measuring the amount of functionally active NSE (NSE-FA) associated with acute brain injury.

Another object of the present invention is to provide a Tethered Enzyme based diagnostic for one or more biomarkers including one or more of the following:
1. NSE-FA,
2. ALT, and/or
3. AST Another object of the present invention is to provide an IVD strip comprising 3 or more wells for use in Tethered Enzyme-based assays where the wells include one or more of the following:
1. Test wells,
2. Positive control wells,
3. Negative control wells, and/or
4. Additional diagnostic wells to provide additional differentiation, e.g. the level of enolase from hemolysis in the sample.

Another object of the present invention is to provide a method for producing one or more of the components of a Tethered Enzyme-based assay, the method including one or more of the following:
1. Nucleic acid-based production of enzymes, which can be followed by purification of the enzyme
2. A process for tethering enzymes to nanoparticles for use in an assay providing specific oriented immobilization that increases the stability and activity of the enzymes to facilitate improved shelf life and shorter detection times than that with non-oriented enzymes, immobilized or not.
3. A process for creating and adding to wells, the mixtures for the assay that prevents premature reaction of the mixtures,
4. A process for freeze drying and packaging the assay to provide a shelf life between hours at room temperature and up to several years in a freezer. A preferred embodiment would have a shelf life of a month at room temperature and a year at normal freezer temperatures.

Still another object of the present invention is to provide for IVD- or PoC-based TET assays, one or more calculations for biomarker measurement based on luminescence from one or more wells including one or more of:
1. Test wells,
2. Positive control wells,
3. Negative control wells, and/or
4. Additional diagnostic wells to provide additional differentiation, e.g. the level of enolase activity introduced from hemolysis in the sample.

Still another object of the present invention is to provide for IVD- or PoC-based TET assays, an algorithm/calculation for biomarker measurement based on the initial reaction rate (slope) of the luminescence data from one or more wells including one or more of:
1. Test wells,
2. Positive control wells,
3. Negative control wells, and/or
4. Additional diagnostic wells to provide additional differentiation, e.g., the level of enolase from hemolysis in the sample.

Still another object of the present invention is to provide an IVD strip with wells shaped to reduce crosstalk and optimize light capture by the photodiode detector or the plate reader.

Still another object of the present invention is to provide a formulation of an IVD or PoC luminescence assay to measure liver enzymes ALT or AST directly from plasma or serum using a sample pre-treatment, for example with uric acid and uricase. In a preferred embodiment the pre-treatment materials would be added to or included in a blood collection container.

Still another object of the present invention is to provide an IVD embodiment having variable numbers of wells that could all fit within a single adaptor for standard plate readers (e.g., 1, 3, 6, 12, 24, 48, 96, 384 wells). Such an embodiment could allow for readings from a single patient for multiple biomarkers (e.g., different RNA sequences that would be specific for different viral pathogens, or different RNA sequences that would be specific for different variants of a single virus, or various analytes of different kinds that together provide a diagnostic panel that reflects the function of a body system or organ, or pathological condition), or from several patients for one or more biomarkers.

Yet another object of the present invention is to provide a point-of-care device capable of running one or more tethered enzyme-based assays having one or more of the following features:
1. Integrated blood draw microsampling capability of up to 1 ml,
2. Integrated blood/plasma separation,
3. Luminescence detection using photodiodes
4. Inclusion of multiple wells/zones including one or more of the following:
   a. Test wells,
   b. Positive control wells,
   c. Negative control wells, and/or
   d. Additional diagnostic wells to provide additional differentiation, e.g., the level of enolase from hemolysis in the sample.
5. Interface to allow connection to one or more microsampling vials,
6. Means to ensure appropriate levels of fluid reach each well/zone
7. Staged assembly of assay components during manufacture such as separation of one or more substrates from the primary tethered enzyme mixture, so that premature activation of the reaction is avoided and all required assay components mix upon reconstitution of the freeze-dried reagents,
8. Staged exposure to one or more assay components during flow of the sample such as separation of one or more substrates from the primary tethered enzyme mixture, and/or
9. Calculation-based measurement of luminescence that can be calibrated to provide quantitative and/or qualitative measurement of biomarkers.

Yet another object of the present invention is an embodiment of TET-PoC designed to detect enolase or other surface-expressed enzymes related to the presence of oral bacteria that predispose or are otherwise linked to tooth decay in children.

Alternate embodiments of the present invention would substitute for the light emission stage of the preferred embodiment to one that results in a change of color, light absorbance, or electrical conductance or resistance.

While the present invention descriptions describe assays for Neuron Specific Enolase, these embodiments are equally appropriate and applicable assays for any active enolase enzyme.

These and other objects and advantages of this invention will become obvious to a person of ordinary skill in this art upon reading of the detailed description of this invention including the associated drawings as presented herein.

BRIEF DESCRIPTION OF THE DRAWINGS

FIG. 1 is a block diagram showing an embodiment of the steps in a three stage TET assay, such as for detection of a biomarker that itself has catalytic enzyme activity.

FIG. 2 is a table showing an embodiment of the lists of well component for TET assays for NSE-FA, and liver function enzymes ALT and AST.

FIG. 3A is a diagram showing an embodiment of the test well components for the assay for NSE-FA FIG. 3B is a diagram showing an embodiment of the process that occurs when a liquid sample containing enzymatically active NSE is inserted into the present invention reaction test well or zone.

FIG. 4A is a schematic view of an embodiment of the TET custom IVD strip designed for placement into the holder for a standard plate reader device.

FIG. 5 is a block diagram of an embodiment of the enzyme production process using bacteria to produce enzymes designed for tethering.

FIG. 6 is a block diagram of an embodiment of the enzyme tethering process.

FIG. 8 is a top view of a preferred embodiment of a production module being a standard 96-well, 8-strip holder with eight empty 12-well strips.

FIG. 9A is a top view of the production module with holder and with the eight strips after a first layer has been deposited into the test and negative control wells.

FIG. 9B is a top view of the production module with the eight strips after completion of sub-process 1 of FIG. 7.

FIG. 9B' is a top view of the production module with eight strips as it would be after step 2-2 of sub-process 2 of FIG. 7.

FIG. 9C is a top view of the production module with eight strips on the freezer block as it would be after completed step 3-1 of sub-process 3 of FIG. 7.

FIG. 9D is a top view of the configuration of the completed production module.

FIG. 10A is a schematic view of the freezer block with depression placed on top of an insulating pad with pedestals to limit the heat flow from the insulating pad to the freezer block so it will remain at a cold temperature during sub-process 3 of FIG. 7.

FIG. 10B is a schematic view of the Freezer block with a handle inserted into slots in the freezer block.

FIG. 13A is a schematic view showing an embodiment of a TET assay card configured for insertion into a photodiode-based reader.

FIG. 13B is a top view showing an embodiment of a TET diagnostic PoC card layout where the fluid input zone is centrally located with 5 blood separation strips leading to five reaction zones.

FIG. 14 is a schematic view of an embodiment of a TET coupled enzyme assay test module where a blood sample volume is deposited into an upper cylinder with strip holder and 4 blood separation paper strips.

FIG. 17 is a block diagram of an embodiment of the electronics module that has features that would be incorporated into either or both electronic module embodiments of FIG. 15 and FIG. 16.

DETAILED DESCRIPTION OF THE DRAWINGS

Figure 3C:
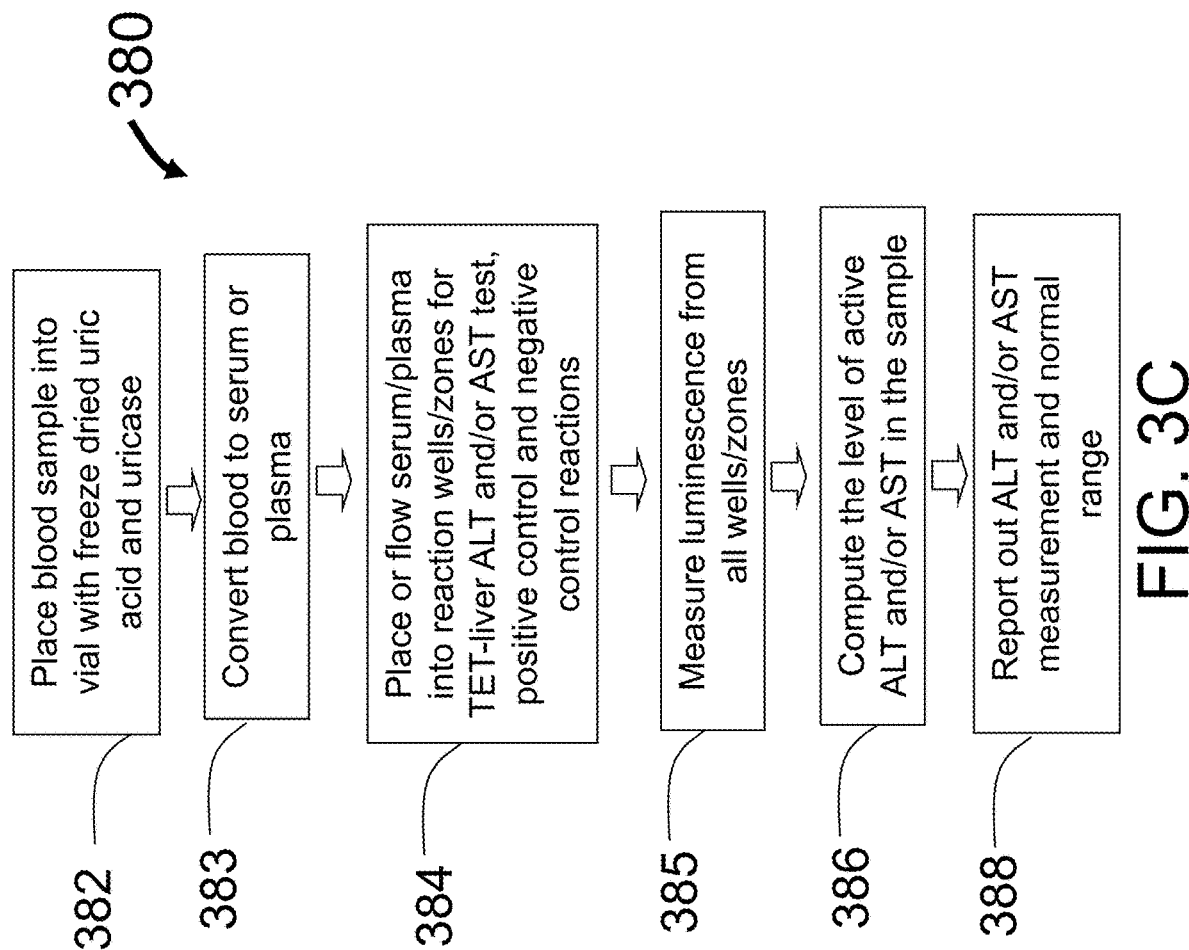
FIG. 3C is a block diagram of an embodiment of the method using tethered enzymes to measure liver enzymes directly from plasma or serum.

FIG. 1 is a block diagram showing an embodiment of the components in the test reaction well for a three stage TET coupled enzyme assay 100. Element P1 110 that may contain an enzyme biomarker E1 103 is a sample of body fluid (e.g., saliva, urine, mucus, blood or plasma/serum) being assayed, the sample 110 being inserted or flowing into a test well or test zone. In an alternate embodiment important for certain assays, for example assays for the liver enzymes ALT and AST, an additive A0 101 is combined with a precursor sample P0 102 to produce the sample P1 110. For assays that do not require a pre-treatment with A0 101, P0 102 is the same as P1 110.

The test well or zone would typically include the following components at the time the enzyme E1 103 is placed in the well or flows into the zone:

SA1 111 and SA2 112 being the one or more substrates/co-factors/reagents on which the enzyme E1 103 acts to produce the one or more reaction products SB1 121 and/or SB2 122, with at least one that will serve as the substrate taken up by the first tethered enzyme nanobot TE1 120. Note that throughout this text and figures, use of the term "substrate" is meant to include any co-factors (inorganic or organic) or other reagents needed for the activity of the relevant enzyme, whether the enzyme is tethered as part of the TET diagnostic system.

TE1 120, the first tethered enzyme nanobot that acts on the output substrate SB1 121 from E1 103 in conjunction with the substrate SB3 123 that is already in the test well or zone to produce the one or more reaction products SC1 131 and/or SC2 132 that can serve as substrates for the second tethered enzyme nanobot TE2 130.

TE2 130, is the second tethered enzyme nanobot that acts on SC1 131 in conjunction with the substrate SC3 133 already in the well or zone to produce the output signal 140. Examples of output signals include light emission, color changes or electrical signals.

Other materials 150 including buffers and cryo-protectants. For example Mg2+, KCl, Ca2+, HEPES, dextran, and/or sorbitol.

While FIG. 1 shows a coupled enzyme assay 100 with two tethered enzymes TE1 120 and TE2 130, it is envisioned that embodiments with only one or with three or more sequential coupled enzymes, each producing at least one needed substrate as input for the next in the sequence can be used, with the last tethered enzyme providing an output similar to the output 140 of TE2 130 shown here.

FIG. 2 is a table showing an embodiment of the lists of reaction well/zone components for TET-IVD or TET-PoC luminescence assays for the enzymes NSE-FA and liver enzymes ALT and AST. In a preferred embodiment of this assay formulation for NSE-FA and liver enzymes, P0 102 and P1 103 are plasma or serum produced from a patient's blood.

The pre-treatment element A0 101 for the liver enzyme assays is a combination of tethered uricase (TET-Uricase) plus uric acid that in a preferred embodiment is frozen or freeze dried either in a tablet, powder or onto the inside surface of a vial used to contain the plasma or serum. When thawed or exposed to liquid the uric acid will act as a substrate to the TET-Uricase to produce Hydrogen Peroxide $H_2O_2$. This pre-treatment step is an important aspect of the present invention as the $H_2O_2$ produced eliminates anti-oxidants from the sample P0 102 before it is added to the well or zone becoming the sample P1, 103. Specifically, without this the anti-oxidants such as ascorbic acid, uric acid, and glutathione, would otherwise diminish the enzymatically produced $H_2O_2$ as input for the final stage of the coupled reaction produced by TE2 130.

It is envisioned that other embodiments of the pre-treatment element A0 101 may include Glutathione s-transferase (GST), superoxide dismutase (SOD), and/or enzymes that are oxidases that following interaction with their substrates create peroxides including hydrogen peroxide. These include:

Uricase without uric acid

Ascorbate oxidase with or without ascorbic acid, and

Glucose oxidase with or without glucose

The initial substrates SA1 111 and SA2 112 on which the enzyme being detected works is 2-PG for NSE-FA and the combination of α-ketoglutarate and L-Alanine for ALT and α-ketoglutarate and L-Aspartate for AST. SB2 122 represents additional outputs of E1 103 that are not used in subsequent reactions SB2 122 of the reaction of ALT is Pyruvate and of AST is Oxaloacetate.

The first tethered enzyme TE1 120 is Pyruvate Kinase (PK) for NSE-FA and Glutamate Oxidase (Glut-Ox) for ALT and AST. An additional input pre-seeded in the well or zone for use with TE1 120 being Pyruvate Kinase is ADP as the substrate SB3 123. The output of the first Tethered enzyme SC1 131 is ATP for the NSE-FA assay and Hydrogen Peroxide ($H_2O_2$) for ALT and AST.

The second Tethered enzyme TE2 130 Is Luciferase for NSE-FA and Horse Radish Peroxidase for ALT and AST. The substrate in the mixture SC3 133 that is worked on by the second tethered enzyme TE2 is Luciferin for NSE-FA and Luminol for ALT and AST.

All three assays produce photons through luminescence as the output signal 140 from the second tethered enzyme TE2 130 being luciferase for NSE-FA and Horse Radish Peroxidase (HRP) for ALT and AST.

FIG. 3A is a diagram showing an embodiment of the well/zone 300 components for the three stage TET assay for functional activity of NSE (NSE-FA). These are the substrates 2-phosphoglycerate (2-PG) 301, Adenosine Diphosphate (ADP) 302, the first tethered enzyme Pyruvate Kinase (TET-PK) 303, Luciferin 304, the $2^{nd}$ tethered enzyme Tethered Luciferase (TET-Luciferase) 305 and other materials 306.

FIG. 3B is a diagram showing an embodiment of the process 350 that occurs when active NSE-FA 310 is introduced into the reaction well 300. The sequential steps are:

Step 351. The functionally active NSE placed in the well or flowing into a zone (NSE-FA) 310 will take up the substrate 2-PG 301 to produce Phosphoenolpyruvate (PEP) 311. The PEP 311 is released into the well/zone where the step 351 will continue so long as there is 2-PG 301 in the well.

Step 352. The first tethered enzyme TET-PK 303 will take up the PEP 311 from step 351 and ADP 302 pre-seeded in the well/zone to produce Adenosine Triphosphate (ATP) 312. The ATP 312 is released into the well/zone where step 352 will continue for the needed measurable time period as long as there is PEP 311 from step 351 and ADP 302 in the well.

Step 353. The second tethered enzyme TET-Luciferase 305 will take up the ATP 312 and Luciferin 304 pre-seeded in the well to produce luminescence (a light output signal) 315 with one photon per ATP 312 molecule. Step 353 will continue for the needed measurable time period as long as there is ATP 312 from step 352 and luciferin 302 in the well.

With each molecule of the NSE biomarker capable of performing at least hundreds of reactions per second, and each nanobot having hundreds to thousands of enzymes tethered to each silica ($SiO_2$) nanoparticle, with an immobilization and enzyme orientation designed to optimize enzyme stability and activity in coupled enzyme reactions, and each of these hundreds to thousands of enzymes producing the reactions of steps 352 or 353, the overall signal production is extremely rapid. The total amount of signal is primarily limited by the amount of activity of the NSE-FA in the sample because no other substrates, co-factors or enzymes are present in limiting quantities for the desired assay time period that is typically less than 10 minutes and ideally less than 3 minutes. The embodiments of the present invention described in the remaining figures also allows excellent dynamic range of detection of the NSE-FA and the ability to directly assay the activity from plasma. While the preferred embodiment would use silica nanoparticles, it is envisioned that other nanoparticles would work so long as the nanoparticle material is transparent, translucent or reflective. For example, such nanoparticles would include:

Polycarbonate, acrylics such as LUCITE®, diamond, ceramics, other polymers, silver, gold and platinum. While nanoparticles typically range in size from 1 nm to 500 nm, it is also envisioned that other sized or non spherical particles may be used.

While the preferred embodiment uses nanoparticles that are approximately spherical, it is envisioned that embodiments using other shapes are possible including the following shapes:

a. Cylindrical including nanowires,
b. Mesoporous,
c. Plates,
d. Oblate spheroids, and
e. Other heterogeneous shapes.

including beads, solid rods or other surfaces, or shapes extending from a surface could be used to stabilize the tethered enzymes.

FIG. 3C is a block diagram of an embodiment of the present invention method 380 to measure liver enzymes ALT and/or AST directly from plasma or serum using embodiments of the present invention tethered enzyme technology. The method 380 begins with step 382 where a blood sample is placed into a vial or container into which freeze dried uric acid and uricase have been added. In a preferred embodiment, the vial has the freeze-dried materials attached to a portion of the inner surface of the vial that is sealed and packaged in preparation for future use. In an alternate embodiment, powder or a tablet containing uric acid and uricase can be separately added to the vial. In other embodiments, the vial would be a vacutainer. In another preferred embodiment, the uricase is in the form of a tethered enzyme where the tethering may be either to the surface of the vial or to another surface such as that of a silica nanoparticle.

Next in step 383 the blood is converted to serum or plasma. In a preferred embodiment it is envisioned that step 383 could be done first where the blood is converted to serum or plasma before it is placed in the vial with uric acid and uricase.

Next in step 384, the serum or plasma from steps 382 and 383 is placed or flowed into one or more test reaction wells or zones having the materials described in FIGS. 1 and 2 for the liver enzymes ALT and/or AST. A portion of the plasma or serum would also be placed in one or more negative control wells or zones where one or more of the initial substrates SA1 111 and SA2 112 shown in FIG. 2 are absent. Finally, a third portion of the plasma or serum would be placed or flowed into one or more positive control wells or zones with the same components as the test wells/zones but also including a pre-seeded amount of the enzyme biomarker (e.g., ALT and/or AST).

While the preferred embodiment uses positive and negative control reactions, it is also envisioned that embodiments of low range and high range reactions could be used.

Figure 11A:
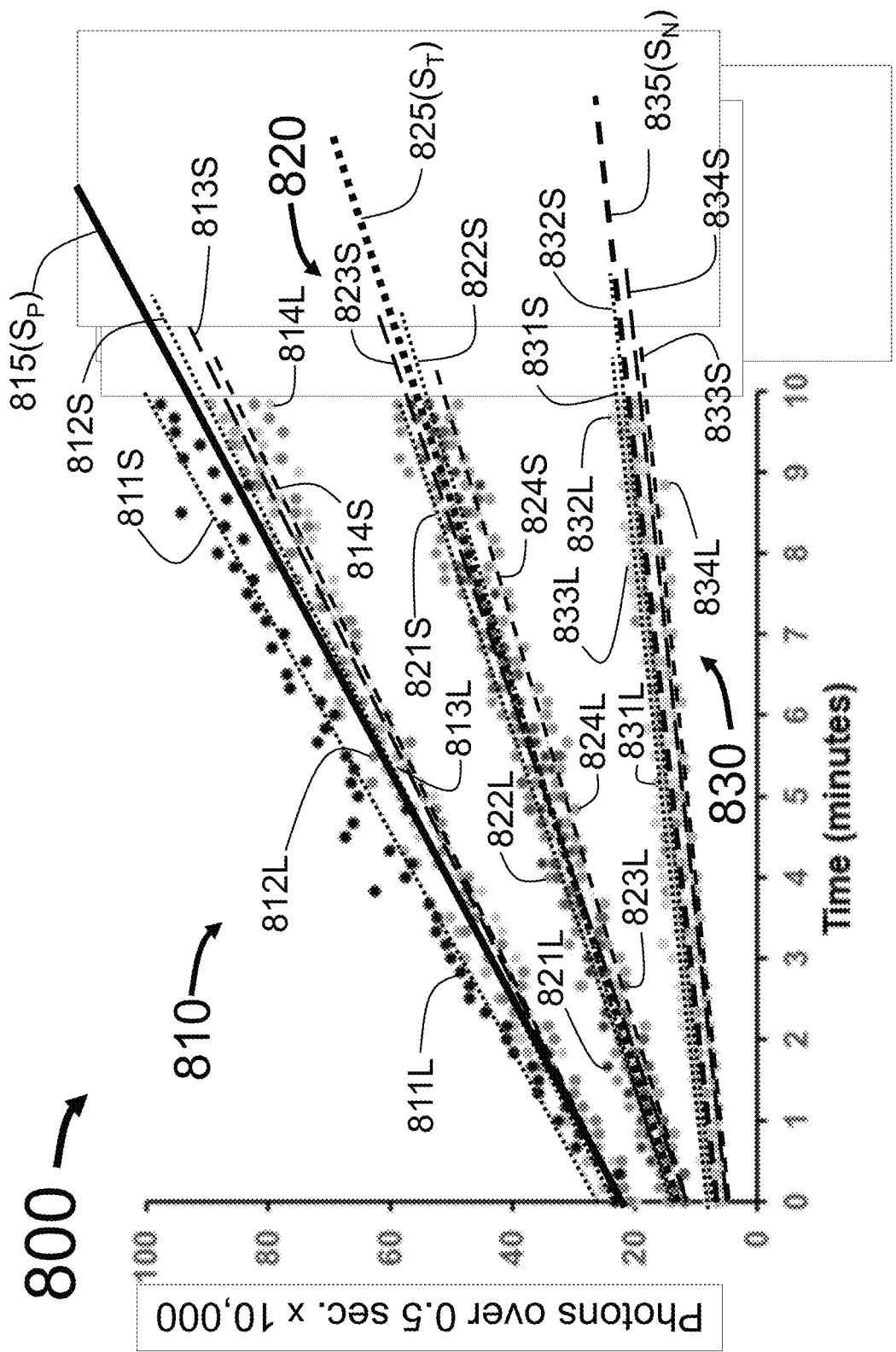
FIG. 11A is a graph showing an example of the luminescence data from a 12-well strip (e.g., the output of an NSE-FA diagnostic strip) following insertion of a patient plasma sample into each well.
Figure 11C:
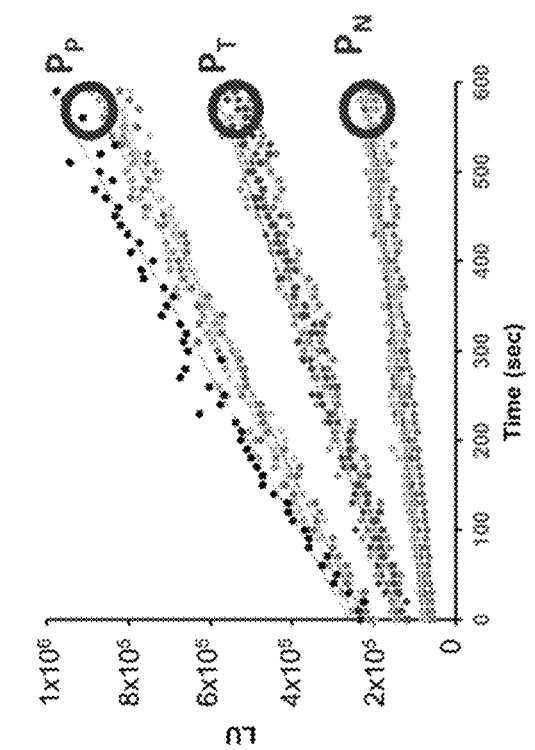
FIG. 11C is a graph showing an alternate algorithmic embodiment to measure luminescence data from a coupled enzyme reaction.
Figure 11B:
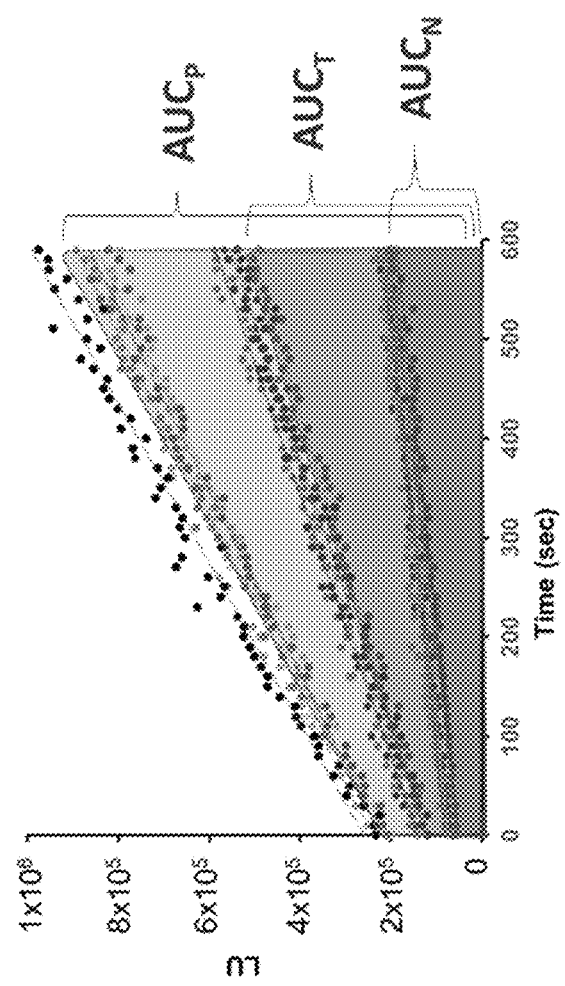
FIG. 11B is a graph showing an alternate algorithmic embodiment to measure luminescence data from a coupled enzyme reaction.

Next in step 385, the luminescence is measured from all the wells/zones and;

In step 386 the level of active ALT and/or AST is computed based on the luminescence measured from the test, positive and negative control wells/zones (e.g., as described with FIGS. 11A, 11B and 11C).

Finally in step 388, the quantitative measurement of ALT and/or AST activity is reported out and may include a display of the normal range of measurement of each.

FIG. 4A is a schematic view of an embodiment of the present invention custom assay strip 400 with 12 wells 402, having tapered (chamfered or filleted) entry 403 with an alignment notch 401 and lip 403. The notch 401 and lip 403 provide guides for placing the 12-well strip into a standard plate reader holder so that the left to right orientation of the wells is proper as the contents of the wells may differ.

Specifically, if test wells, as well as negative and positive control wells are used in a non-symmetric layout, the proper orientation of the strip 400 is critical to interpret results. Note that in preferred embodiments for a luminescence readout, these 12-well strips crafted individually or produced as a portion of a 96-well plate, would be made of a white or reflecting materials so that more photons will leave the well and be captured by a plate reader or photodiode-based device. The image in FIG. 4A is shaded to provide easier viewing.

Figure 4B:
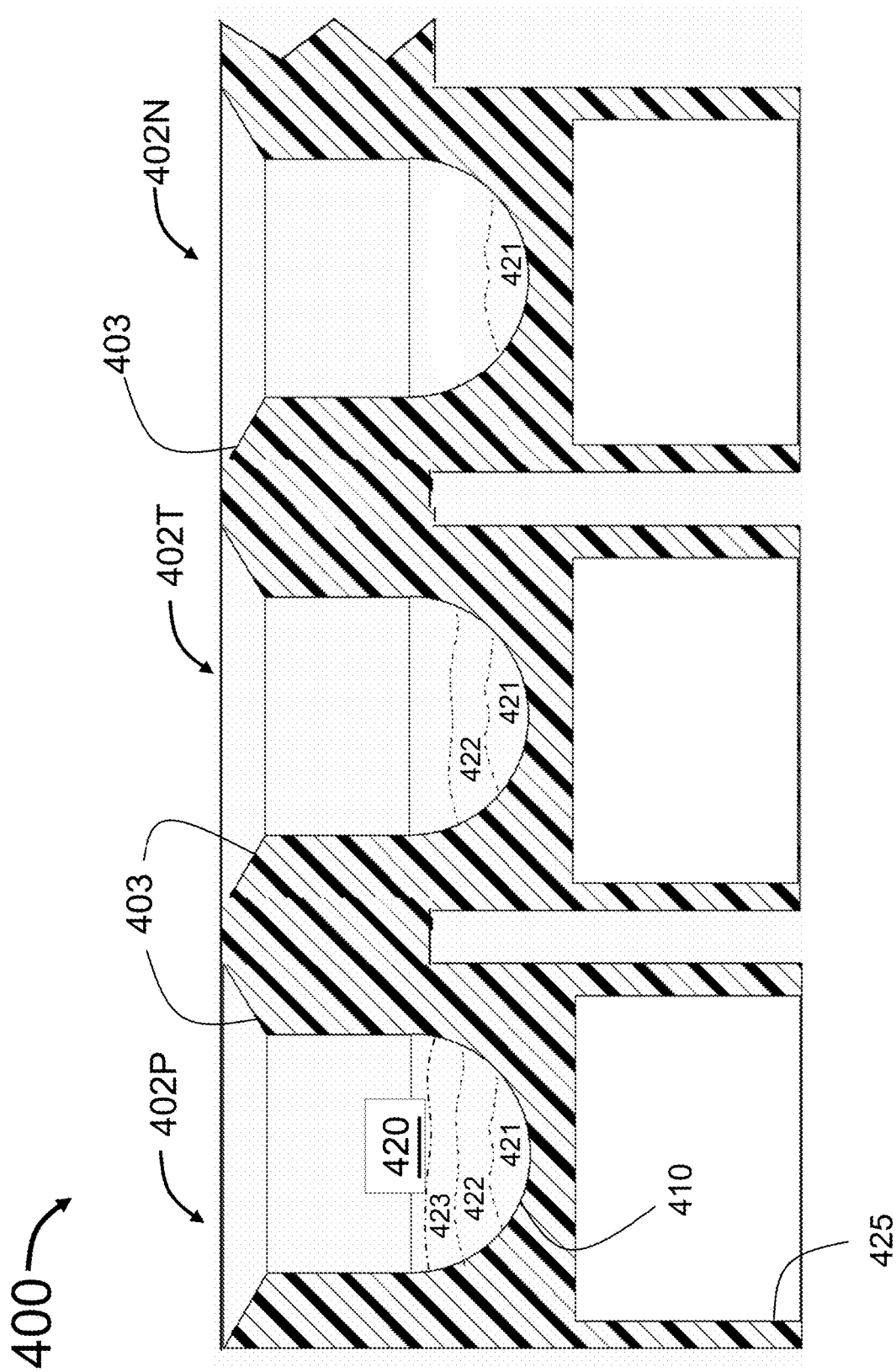
FIG. 4B is a cross sectional view of an embodiment of the shape of the wells in the strip of FIG. 4A showing the three layers of components of reaction test and positive control wells.

FIG. 4B is a longitudinal cross sectional view of a portion of a three layer component embodiment of the 12-well strip 400 of FIG. 4A showing a test well 402T, a positive control well 402P and a negative control well 402N, each well having a tapered entry 403 and a well volume 420, a curved bottom 410 and underside inset 425 to reduce the amount of plastic needed. The test well 402T has two layers of freeze-dried components 421 and 422 while the positive control well has three layers 421, 422 and 423. The negative control well 402N has only one layer 421. The layer 423 would include a pre-set amount of the biomarker being assayed with examples being an enolase for the NSE-FA assay and ALT or AST for the assays of liver enzymes. The positive control is key to the ability to quantify the enzymatic activity of the biomarker in the patient sample being assayed.

In a preferred embodiment where the biomarker is an enzyme, layer 423 would include the biomarker tethered to silica nanoparticles.

In an embodiment, the 12-well strip 400 would have at least one set of the three wells shown with alternate embodiments of 2 sets, 3 sets or 4 sets. It is also envisioned that other combinations such as one negative control 402N, three positive control wells 402P and three test wells 402T can be used.

In the embodiment where the strip 400 is used for the assay for functionally active NSE-FA shown in FIGS. 3A and 3B, an embodiment is to have the layer 421 include all the components shown in FIG. 2A except the 2-PG substrate 301. The layer 421 is placed in all the wells including test well 402T, negative control well 402N and positive control well 402P. During manufacturing, the layer 421 is placed into the well and then frozen.

For the NSE-FA embodiment of the strip 400 of FIG. 4B, the layer 422 would include the substrate 2-PG 301 of FIG. 3A and would be placed on top of the frozen layer 421 in the test wells 402T and positive control wells 402P but not the negative control wells 402N. Once inserted this layer would also be frozen. The layer 423 for the NSE-FA assay would include a pre-set amount of an active enolase and would be placed only in the positive control wells 402P and quickly frozen to prevent reaction with the frozen 2-PG in layer 422.

In a preferred embodiment one or more 12-well strips 400 would be placed on a freezer block to maintain the frozen state of the components when layers 422 and 423 are added. In a preferred embodiment, the freezer block such as the freezer block 490 of FIG. 10A would be designed to hold eight strips either individually or in a separate holder.

After all layers are deposited and then frozen, the strip(s) 400 are placed in a lyophilizer to freeze dry the strip(s) 400 that are then sealed in a light blocking and moisture resistant pouch that may optionally include a desiccant as any water that reaches the positive control well 402P could trigger premature reaction.

Figure 7:
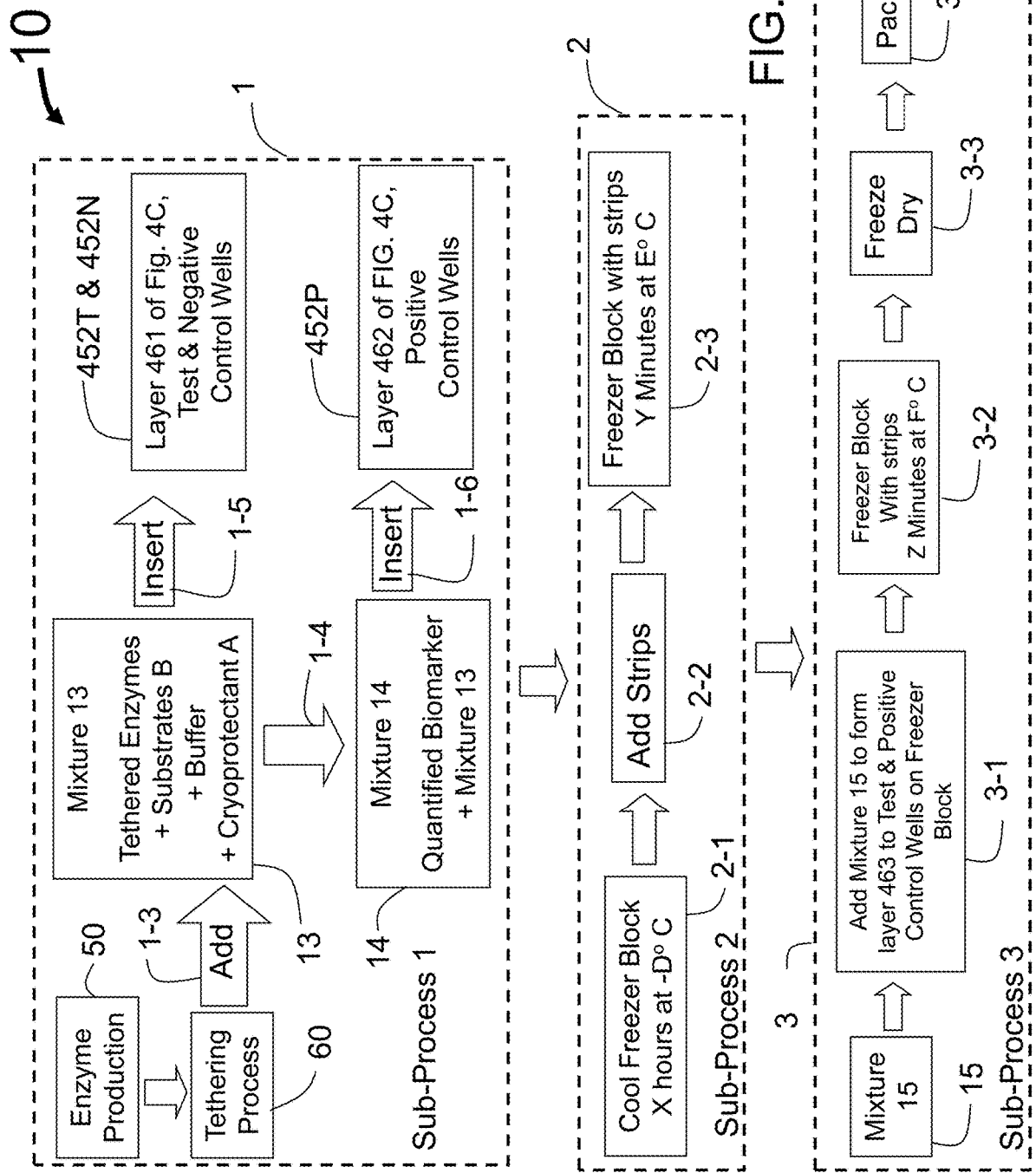
FIG. 7 is a block diagram of an example of a preferred embodiment of the production process for the assay strips of FIG. 4A, including the steps for inserting the materials that are placed into the wells/zones for the present invention TET coupled enzyme assay of FIG. 1.

In an alternate embodiment to the layers 421, 422 and 423 may be placed in the wells in a different order with the biomarker (e.g. enolase) layer 423 placed first in the positive control wells, the primary component group 421 without 2-PG 301 placed next in all wells and the 2-PG 301 layer 422 placed last in the treatment wells 402T and positive control wells 402P. FIG. 7 describes a preferred embodiment of the process for laying down the layers to prevent inadvertent reaction.

It is also envisioned that if a fourth type of well being a second type of negative control well is used, then there would be three sets of four wells. An embodiment of such an added negative control is having a test well that includes a suppressant for NSE-FA but will still react to other forms of enolase from other sources including hemolysis.

Figure 4C:
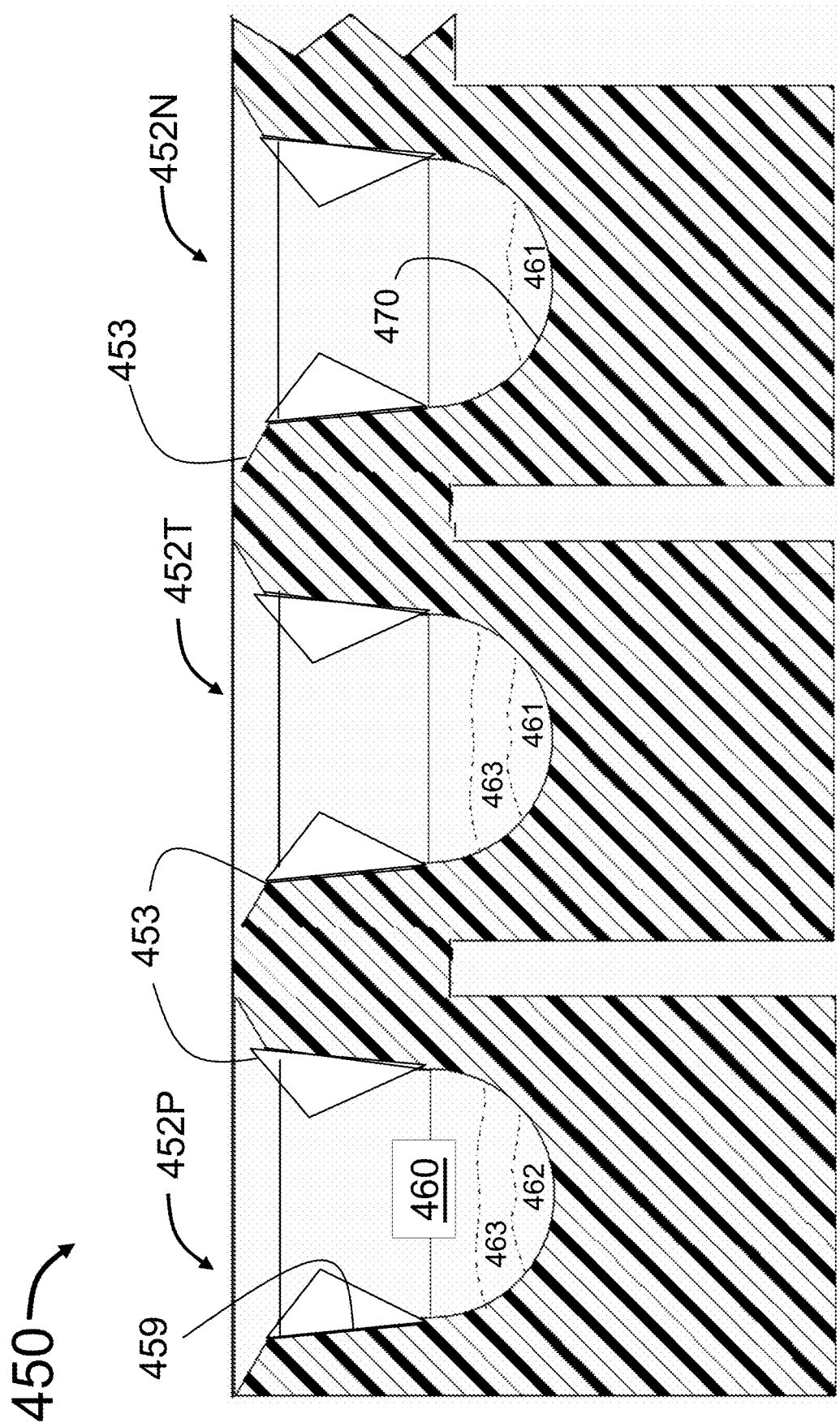
FIG. 4C is a cross sectional view of a preferred embodiment showing the shape of three wells in a strip with two layers shown for positive control, test and negative control wells.

FIG. 4C is a cross sectional view of a two layer preferred embodiment of the present invention coupled enzyme assay showing the shape of three wells of a 12-well strip 450 with positive control well 452P, test well 452T and negative control well 452N. Each well having a tapered entry 453, a tapered upper well 459, a well volume 460 and a curved well bottom 470. The positive control well 452P has two layers of freeze-dried components 462 and 463. The test well 452T, similar to the test well 402T of FIG. 4B, has two layers of freeze dried components 461 and 463 while the negative control well 452N, similar to the negative control well 402N of FIG. 4B, has only one layer 461. The advantage of a tapered well top 459 is to better allow for mold release without use of chemicals.

In the embodiment where the strip 450 is used for the assay for functionally active NSE-FA described in FIGS. 3A and 3B, a preferred embodiment is to have the layer 461 include all the components shown in FIG. 2A except the 2-PG substrate 301. Layer 461 is placed in test wells 452T and negative control wells 452N.

In the embodiment where the strip 450 is used for the assay for ALT or AST described in FIG. 3C, a preferred embodiment is to have the layer 461 include the components Luminol and L-Alanine for ALT and Luminal and L-Aspartate for AST. Layer 461 is placed in test wells 452T and negative control wells 452N.

The layer 462 in the positive control wells would include the components in layer 461 plus a preset amount of the biomarker desired (e.g. an Enolase for the NSE-FA Assay, ALT or AST for liver enzyme assays). Layer 462 would be placed as a first layer of each positive control wells 452P. In a preferred embodiment where the biomarker is an enzyme, layer 462 would include the biomarker tethered to silica nanoparticles. For the NSE-FA embodiment the layer 423 would include an enolase tethered to silica nanoparticles.

After the first layer (461 or 462) is deposited, the entire strip 450 is placed in a freezer for a specified time between 1 and 30 minutes in a −15° to −100° C. freezer, with a preferred embodiment being for at least 15 minutes in a less than −70° C. (e.g. a −80° C.) freezer.

In a preferred embodiment, eight strips would be placed into a multi-strip holder, layers 461 and 462 would be placed into in the wells at temperatures between 4° C. and 25° C. then a freezer block described (e.g., 490 of FIGS. 9B', 9C, 10A and 10B) would be removed from a freezer and the multi-strip holder (e.g., 485 of FIG. 8) with the strips 450 would be placed onto the freezer block 490 and frozen at −15° to −100° C. for 5 to 30 minutes with a preferred embodiment being for at least 15 minutes in a less than −70° C. (e.g. a −80° C.) freezer.

After removing the frozen strip(s) 450 from the freezer, the second layer 463 is placed on top of the frozen first layer 461 in the test wells 452T and on top of the frozen first layer 462 of the positive control well(s) 452P but not the layer 461 of the negative control well(s) 452N. Once deposited, layer 463 would then be frozen for a specified time between 1 and 30 minutes in a −15° to −100° C. freezer, with a embodiment being for at least 15 minutes in a less than −70° C. (e.g. a −80° C.) freezer.

For the embodiment for NSE-FA, layer 463 would include the substrate 2-PG of FIGS. 3A and 3B as well as buffers and cryoprotectants. For the embodiment for ALT and AST the layer 463 would include the substrate α-ketoglutarate as well as buffers and cryoprotectants.

After all layers are deposited and then frozen, the strip(s) 450 are placed in a lyophilizer to freeze dry the strip(s) 450 that are then sealed in a light blocking and moisture resistant pouch that may optionally include a desiccant as any water that reaches the positive control well 452P could trigger premature reaction.

In a preferred embodiment where the biomarker is an enzyme, layer 462 would include the biomarker tethered to silica nanoparticles. For the NSE-FA embodiment the layer 462 would include an enolase tethered to silica nanoparticles.

In an alternate embodiment the layers may be placed in the wells in a different order with the layer 463 placed first in the positive control well(s) 452P and test well(s) 452T and the strip frozen. Then the layer 462 of the positive control well(s) 452P and the layer 461 of the test and negative control wells 452T and 452N would be added.

While the layers can be reversed, a preferred embodiment of the present invention has layer 463 that includes the substrates with which the enzyme biomarker reacts on top of the base layers 462 and 461 so layer 463 is that the first layer contacted when the sample is placed in the well. This facilitates a faster reaction start up allowing for better and quicker separation of the luminescence curves the test and positive control reactions.

FIG. 5 is a block diagram of a preferred embodiment of the enzyme production process 50 using an expression system (e.g. bacteria) to produce enzymes designed for tethering.

The process begins by identification in step 51 of the specific gene that encodes expression by bacteria of the desired enzyme with affinity tags for tethering.

The gene in fusion with affinity tags to allow tethering as shown in FIG. 6 and purification in step 56 is synthesized in step 52, for example, using a DNA synthesizer.

Next one inserts in step 53 the gene with one or more affinity tags into an expression plasmid/vector.

Next, one inserts the expression plasmid in step 54 into a protein expression system. Examples of expression systems include bacteria, insect cells, mammalian cells, yeast or other known expression systems. Bacteria are used in the preferred embodiment of the process 50.

Next in step 55 the bacteria are induced to produce/express the desired enzyme including the desired affinity fusion tags.

The final step is the purification process 56 that is used to separate other materials from the desired enzymes.

FIG. 6 is a block diagram of an embodiment of the enzyme tethering process 60 where active enzymes are tethered to nanoparticles (e.g., silica ($SiO_2$) nanoparticles) using oriented immobilization that increases the stability and activity of the enzymes to facilitate improved shelf life and faster reaction times than can be achieved with non-oriented enzymes. This novel process produces an oriented immobilization that improves substrate access to the substrate-binding site/active site of each enzyme molecule and/or enables improved conformational changes or movements, and/or improves substrate channeling to a subsequent reaction step. The tethering process 60 follows enzyme purification step 56 of the Enzyme Production Process 50 of FIG. 5 as follows:

The process begins in step 61 by cooling the nanoparticles in a vessel to a temperature between 1 and 10 degrees Celsius.

Next in step 62, the purified enzymes with the affinity tags are added to the vessel.

Next in step 63 the cooled vessel is allowed to incubate for a pre-set period of time. For example a period of 15 to 60 minutes may be used.

Next in step 64 while still cooled, the incubated mixture is washed to remove un-tethered enzymes. For example. the nanoparticles are spun down using a centrifuge to the bottom of the vessel and the remaining liquid is replaced with a buffer such as phosphate buffer. This is repeated 1 to 5 times. In a preferred embodiment, the spin-down speed should for example be between 300 g to 1000 g. In some cases, 2 or more different enzymes may be combined in step 62 where it is desired that more than one type of enzyme is tethered to each nanoparticle. It is also envisioned that one can control the number of enzymes per nanoparticle by controlling the amount of enzymes added in step 62 relative to the size, number and concentration of nanoparticles.

In the final step 65, stabilizers are added to the tethered nanoparticles. For example, suitable stabilizers include sorbitol, dextran, polyethelyne glycol or trehalose, among others.

It is envisioned that nanoparticles with other composition (other than silica) or other structures may also be used with the tethering process 60 to provide a surface for tethering enzymes.

Figure 16:
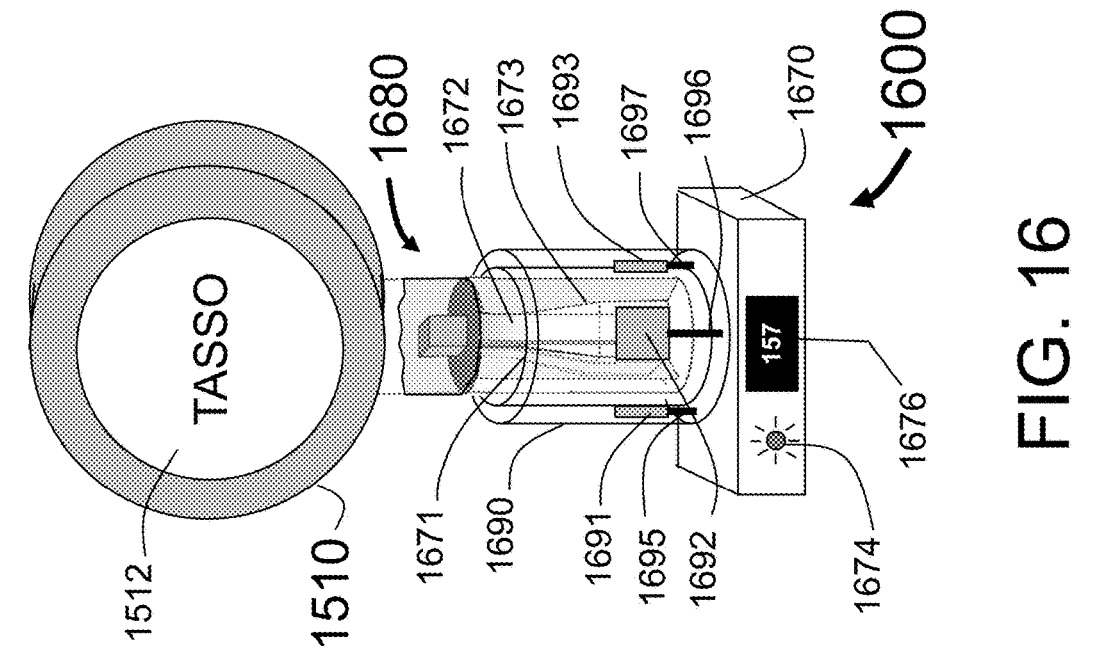
FIG. 16 is a schematic view of an integrated and fully disposable point-of-care TET coupled enzyme assay system including a TASSO blood collection device.
Figure 15:
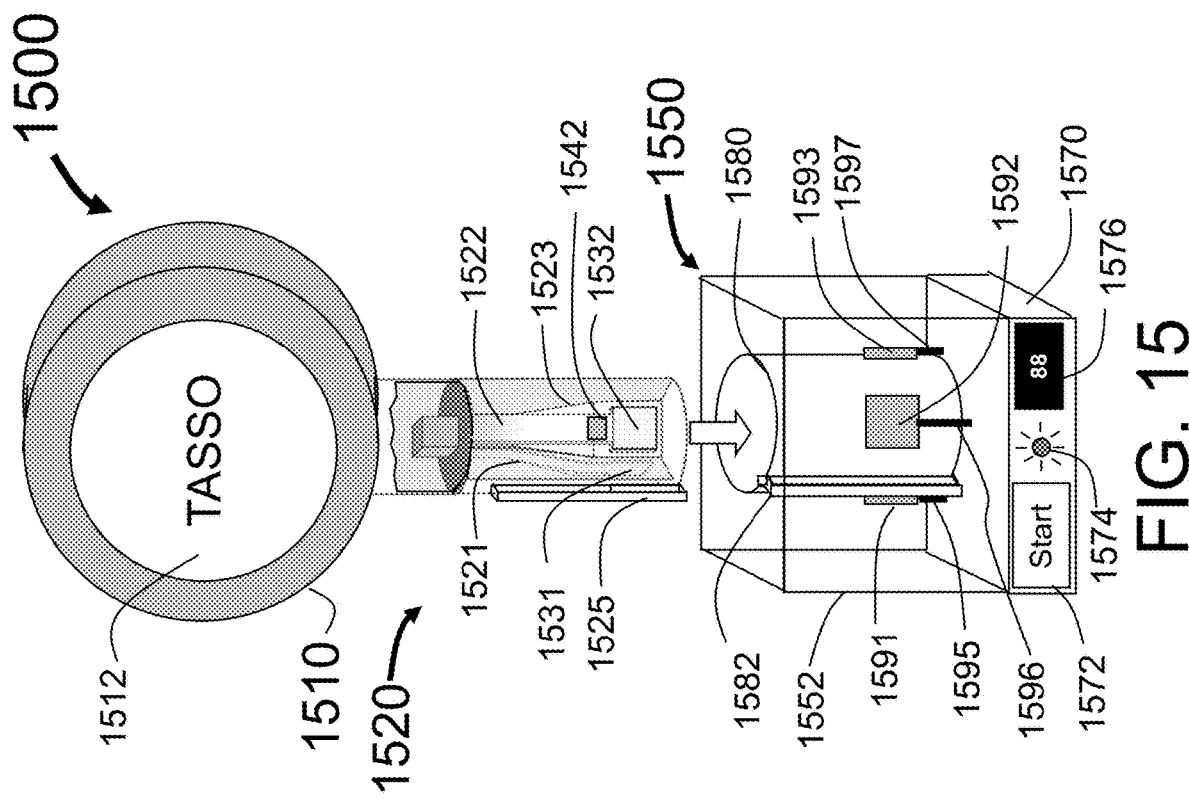
FIG. 15 is a schematic view of an embodiment of a two-piece TASSO/TET assay system with a photodiode luminescence reader (PLR) and the TASSO blood collection device and the normal collection vial replaced by an embodiment of the TET coupled enzyme assay test module similar to the test module of FIG. 14 but with the addition of the alignment key.
Figures 18, 19:
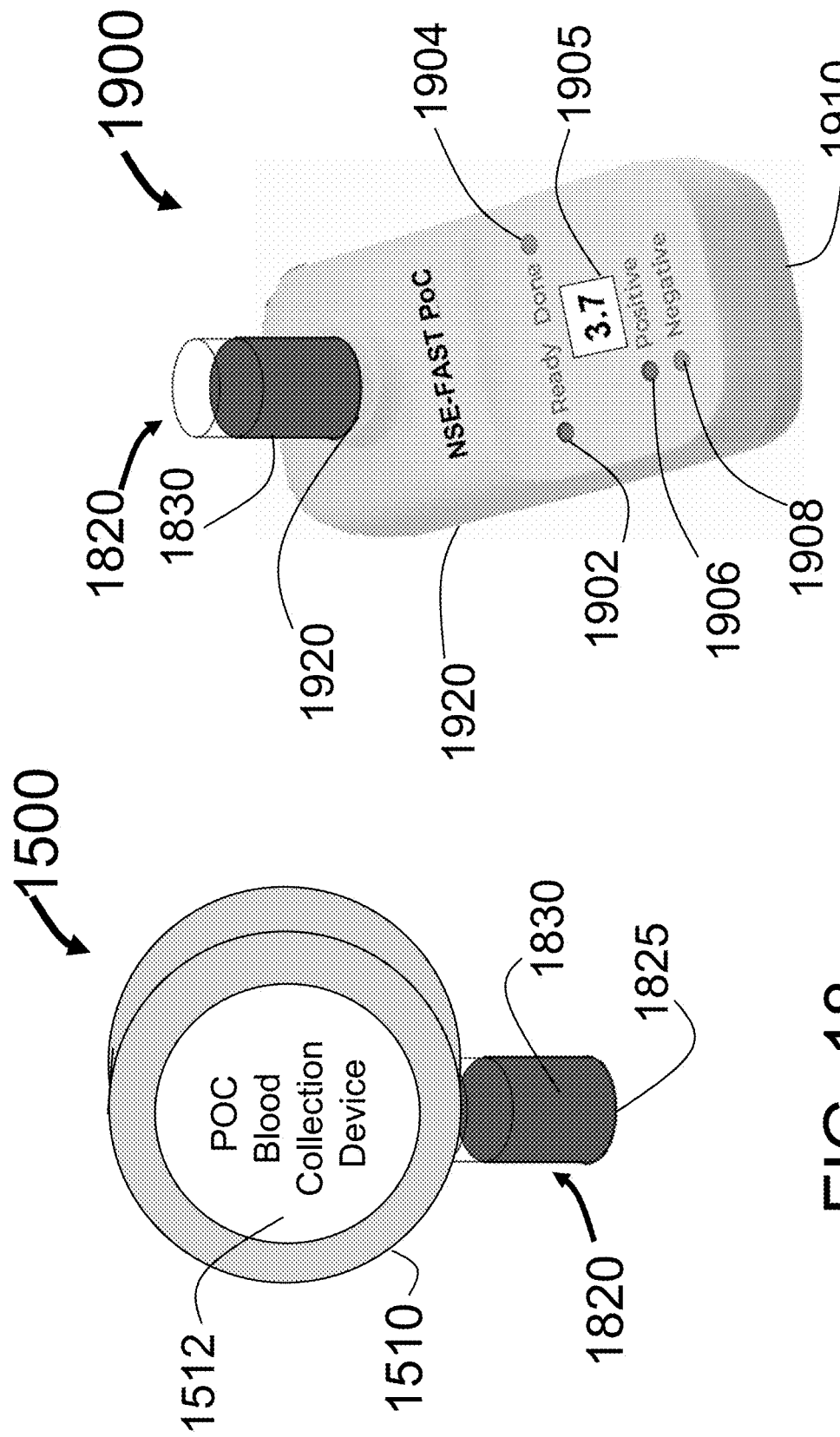
FIG. 18 is a schematic view showing a preferred embodiment of a point of care blood collection device such as the TASSO with body, blood collection activator and microtainer shown with collected blood and bottom surface suitable for needle penetration.
FIG. 19 is a schematic view showing a preferred embodiment of a disposable NSE functional activity stroke test (NSE-FAST) assay.

FIG. 7 is a block diagram of an example of a preferred embodiment of the production process 10 for the assay strips 400 of FIG. 4A, including the steps for inserting the materials that are placed into the wells/zones for the present invention TET coupled enzyme assay 100 of FIG. 1. Such an assay is designed to receive a sample that may include the enzyme biomarker being assayed and can be read using standard lab plate readers (e.g. the TECAN Infinite 200 PRO), a photodiode based reader as shown in FIGS. 15 and 16, or by a reader integrated into a TET-PoC point of care assay device as shown in FIG. 19. A preferred embodiment of the mixture 13, mixture 14 and mixture 15 of FIG. 7 form respectively the layers 461, 462 and 463 of FIG. 4C.

A preferred embodiment of the present invention TET coupled enzyme assay would include at least one test well or zone, at least one positive control well or zone and at least one negative control well or zone.

A preferred embodiment of the present invention production process 10 to produce the strip 450 of FIG. 4C begins with sub-process 1 where a preferred embodiment process is performed at 4 degrees Centigrade comprising the following steps 1. The first step is the enzyme production process 50 of FIG. 5;
2. Next is the enzyme tethering process 60 of FIG. 6;
3. The tethered enzymes are then added in step 1-3 to the other materials including buffers, cryoprotectants and the substrates SB3, and SC3 shown in FIG. 1. These together form mixture 13 being the mixture used as the only layer for the negative control well(s) and the base layer for the test well(s) (e.g. layer 421 of FIG. 4B or layer 461 of FIG. 4C). Examples of the buffers and cryoprotectants include sorbitol, dextran, trehalose, glycerol; potassium ions, magnesium ions, phosphate ions, sodium Ions and/or PEG. For an embodiment of the NSE-FA assay of FIG. 3A, mixture 13 includes ADP (SB3) and luciferin (SC3) but does not include SA1 the primary initial substrate 2-PG needed to start the coupled enzyme reaction once in contact with a patient sample having NSE-FA.

4. Next in step 1-4 a portion of mixture 13 is added to a quantified amount of the biomarker being assayed to form Mixture 14. This is the base layer 462 of FIG. 4C for the positive control well(s). For the NSE-FA assay, the quantified biomarker added is an enolase that in a preferred embodiment may be tethered.

5. At this point, once mixtures 13 and 14 are ready, in step 1-5 a pre-set quantity of the negative control mixture 13 is inserted as layer 461 into the test well(s) 452T and negative control well(s) 452N of FIG. 4C.

6. This is followed in step 1-6 where the mixture 14 is inserted as Layer 462 into the positive control well(s) 452P of FIG. 4C or zone(s) completing sub-process 1.

Sub-process 1 is followed by sub-process 2 with steps as follows:

1. First in sub-process 2-1 a freezer block (e.g., the freezer block 490 shown in FIGS. 10A and 10B), is placed in a freezer for at least X hours at −D degrees centigrade. The freezer block 490—for example might be a piece of aluminum adapted to hold one or more strips 400 of FIGS. 4A-4C or blood separation chromatography strips (e.g., the strips 900 of FIG. 12A. In a preferred embodiment, X is typically more than 6 hours and D is less than −15 degrees centigrade with a preferred embodiment being 24 hours and less than −70 degrees centigrade (e.g. a −80° C. freezer).

2. Next in step 2-2 the freezer block is removed from the freezer and the strips prepared with negative control, test and positive control first layers (e.g., layer 461 and 462 of FIG. 4C) are placed in contact with the freezer block. In a preferred embodiment up to eight 12-well strips are in a holder (e.g., the holder 485 in FIG. 8 for the 8 IVD strip 400 of FIG. 4A).

3. Next in step 2-3, the freezer block with strips is placed back in a freezer for Y minutes below E degrees centigrade. In one embodiment Y is more than 10 minutes and E is −15 degrees centigrade. In a preferred embodiment, Y is 20 minutes and E is −70 degrees centigrade (e.g. a −80° C. freezer). This completes sub-process 2.

The final sub-process 3 in the preferred embodiment for in the production of the present invention coupled enzyme assay comprises the steps as follows:

1. Once the first layers (e.g. 461 or 462 of FIG. 4C) are fully frozen and the strip(s) are still in contact with the freezer block, in step 3-1 of sub-process 3, Mixture 15 is inserted to form layer 463 of FIG. 4C for the positive control well(s) 452P and the test well(s) 452T of FIG. 4C. Mixture 15 includes the substrate(s) that will react with the enzyme biomarker being assayed to begin the reaction ending in a signal output (e.g. the production of luminescence). For the NSE-FA assay, Mixture 15 would include 2-PG. For liver enzymes ALT and AST, Mixture 15 would include α-ketoglutarate. Mixture 15 may also include buffers and cryoprotectants (e.g. sorbitol, dextran, trehalose, glycerol and PEG).

2. Next in step 3-2, the freezer block with the complete formulation for the assay wells or zones, is placed back in the freezer for Z minutes at below F degrees centigrade. In an embodiment Z may more than 10 minutes and F is −15 degrees Centigrade. In a preferred embodiment, Z is 20 minutes and F is −70 degrees centigrade (e.g. a −80° ° C. freezer).

3. Next, in step 3-3, the strip(s) 450 of FIG. 4C with the fully frozen complete formulation of test well(s) 452T, negative control well(s) 452N and positive control well(s) 452P, is placed in a freeze dryer to remove all water or other liquid in the well(s) that could allow the positive control well(s) to begin reacting without the addition of the patient liquid sample(s) to be tested.

4. The final step 3-4 is to remove the strips from the freeze dryer in a low humidity environment and package them in a sealed pouch. In a preferred embodiment a desiccant is placed in the pouch to ensure that no moisture reaches the well(s).

It is also envisioned that the positive control well(s) could be prepared with only the end stage substrates SC3 113 and SC1 131 needed for activation of the signaling tethered enzyme TE2 130 of FIG. 1. For the NSE-FA coupled enzyme assay, this would have the positive control with a first layer including tethered luciferase and luciferin and a second layer with a pre-set quantity of Adenosine Tri-Phosphate (ATP). Similarly, a positive control with the first layer being the composition of the negative control layer 461 of FIG. 4C with a second layer including a pre-set amount of the substrate SB1 121 of FIG. 1 that would be Phosphoenolpyruvate (PEP) for the NSE-FA assay.

It is also envisioned that there could be two or more positive control types with one with the amount of the biomarker (e.g., enolase) at the threshold for brain injury and one at say ten times that to provide calibration and enhance quantification between the two levels.

In another embodiment, the positive control well(s) can be replaced by previously-obtained, temperature-dependent luminescence data recorded from positive controls, or the TET-IVD strip could include an LED that provides a light output over time that may be temperature adjusted to emulate the result that is seen by recorded positive control wells when activated. It is also envisioned that the recorded signal from a positive well could be stored in the TET-PoC memory and no positive well(s) would be needed.

In another embodiment for the point of care TET-PoC NSE-FA assay with electrical voltage signal output, the tethered luciferase (LUC-NP) is replaced by the enzyme Pyruvate Oxidase tethered to silica nanoparticles (PYROX-NP), for preparation of the test wells, and positive control and negative control wells, otherwise the multi-step process is highly similar.

In another embodiment for electrical signal output Pyruvate Oxidase would be tethered directly onto an electrode (preferably silver or gold). the Si-tag will be replaced with Ag-tag or Au-tag.

In another embodiment, The Pyruvate Oxidase will be tethered to $SiO_2$ nanoparticles or to an electrode, and HRP will be immobilized onto an electrode (using e.g., Au or Ag tags). It is also envisioned that cofactors FAD and TDP could be added (but not required).

While it is possible to produce 1 strip at a time, this is not practical for the size and scope of the unmet need for the advanced assays possible with the present invention. The next figures and description will describe a production method to produce multiple strips efficiently for commercial or clinical applications. This technique is also applicable to production with an automated or semi-automated injection system such as the Opentrons OT-2 Workstation.

FIG. 8 shows a top view of a preferred embodiment of a production module 480 being a standard 96-well, 8-strip holder 485 with eight empty 12-well strips 411 through 418. The benefit of the holder 485 is that it allows easy handing during production of eight strips at a time and similarly is designed to be used in standard medical fluid handling devices for production, testing and also in the final use with one or more strips in a medical testing lab. It is also envisioned that embodiments of the present invention can function with as few as 3 wells (i.e., a test well, a positive control well and a negative control well). Thus while the holder 485 shows eight 12-well strips, it could instead hold sixteen 6-well strips or thirty-two 3-well strips.

Note that strips can be manufactured in various configurations (e.g., one or more negative control wells in a row, followed by one or more test wells in a row, followed by one or more positive control wells in a row; or one or more test wells, followed by one or more negative controls, followed by one or more positive controls, etc.). FIG. 9A is a top view of the production module 480A with holder 485 with the eight strips 411A-418A after layer 461 of FIG. 4C has been deposited into the test and negative control wells. Here, for illustrative purposes, we show a pattern of one positive control well, followed by one test well, followed by one negative control well, with this triplet pattern repeating four times in a 12-well strip. Specifically in strip 411A, Layer 461 of FIG. 4C is shown in the four test wells 411AT1, 411AT2, 411AT3 and 411AT4 and four negative control wells 411AN1, 411AN2, 411AN3 and 411AN4. The positive control wells 411AP1, 411AP2, 411AP3 and 411AP4 are still empty at this stage. There are similar deposits in the test and negative control wells for the other 7 strips 412A through 418A.

FIG. 9B is a top view of the production module 480B with holder 485 with the eight strips 411B-418B after completion of sub-process 1 of FIG. 7 where Layer 462 of FIG. 4C has been deposited into the positive control wells. Specifically in strip 411A, Layer 462 of FIG. 4C is shown in the four positive control wells 411AP1, 411AP2, 411AP3 and 411AP4. There are similar deposits in the positive control wells for the other seven strips 412B through 418B. Up to this point, the process can be performed at temperatures between 4 degrees C. up to room temperature.

FIG. 9B' is a top view of the production module 480B' with holder 485 with eight strips 411B-418B as it would be after step 2-2 of sub-process 2 of FIG. 7 where the production module 480B is placed in a rectangular depression 495 in the top of the freezer block 490 after the freezer block 490 has been removed from a freezer (not shown) after step 2-1 of FIG. 7. In this configuration, the production module 480B' with the holder 485 and freezer block 490 is re-inserted into a freezer for Y minutes at E degrees C. as shown in step 2-3 of FIG. 7.

FIG. 9C is a top view of the production module 480C with holder 485 with eight strips 411C-418C on the freezer block 490 as it would be after completed step 3-1 of sub-process 3 of FIG. 7 where the production module 480B' including the freezer block 490 has been removed from the freezer completing sub-process 2 and has then received the final Layer 463 of FIG. 4C where mixture 15 of FIG. 7 has been deposited into the positive control and test well. Specifically in strip 411C, Layer 463 is shown in the four positive control wells 411CP1, 411CP2, 411CP3 and 411CP4 and four test wells 411CT1, 411CT2, 411CT3 and 411CT4. The four negative control wells are skipped in this step. In this configuration, the production module 480C with freezer block 490 is re-inserted again into the freezer for Z minutes at F degrees C. as shown by step 3-2 of FIG. 7.

FIG. 9D is a top view of the configuration of the completed production module 480D after steps 3-2 and 3-3 of FIG. 7, now removed from the freezer block 490 of FIG. 9C and cycled through a freeze dryer to lyophilize the contents of the wells. In this configuration, the holder 485 and eight strips 411D-418D have been removed from the freezer block 490 in a low humidity environment and are ready for removal from the holder 485 and insertion and sealing into light and moisture proof pouches. In a preferred embodiment a desiccant pack/module is inserted into the pouch enclosing the freeze dried strip to ensure no moisture reaches the positive control wells, that will begin to react once wet.

In this configuration, there are four positive control wells, four test wells and four negative control wells ready for use with samples from a patient. For example, for strip 411D, the wells 411DP1, 411DP2, 411DP3 and 411DP4 are positive control wells, the wells 411DT1, 411DT2, 411DT3 and 411DT4 are test wells and the wells 411DN1, 411DN2, 411DN3 and 411DN4 are negative control wells.

The embodiment of FIG. 9D shows the 12 well configuration of PTNPTNPTNPTN where P is a positive control well, T is a test well and N is a negative control well. It is also envisioned that other embodiments of different orders of wells would be viable including NNNNTTTTPPPP, TTTTPPPPNNNN, PPPPTTTTNNNN as well as TTPPNNTTPPNN etc. Also if 3, 6 or 9 wells are needed layout embodiments are envisioned such as NNTTPP, PPTTNN PTNPTN, NNNTTTPPP, PPPTTTNNN, PTNPTNPTN etc. It is also envisioned that using the test well without either or both positive and negative controls could be functional.

FIG. 10A is a schematic view of the freezer block 490 with depression 495 placed on top of an insulating pad 500 with pedestals 502 to limit the heat flow from the insulating pad to the freezer block 490 so it will remain at a cold temperature during sub-process 3 of FIG. 7 when layer 463 of FIG. 4C is added. This will ensure that layer 462 of FIG. 4C of the positive control wells will remain frozen and not start the reaction as the liquid of layer 463 is placed on top of layer 462. The freezer block 490 includes slots 496 and 497 to allow insertion of a handle 499 of FIG. 10B to facilitate moving the freezer block into and out of the freezer and freeze dryer during sub-process 2 and sub process 3 of FIG. 7. It is envisioned that other embodiments of the handle could work including detents on the side of the freezer block 490 to allow a separate tongs to lift from above or a permanent rotatable handle that would rotate to the side lying flat during production and be rotatable to a position to allow the block 490 to be grabbed with gloves.

FIG. 10B is a schematic view of the Freezer block 490' with the handle 499 inserted into the slots 496 and 497. Ideally the handle 499 is made of a material with low thermal conductivity such as wood or plastic. This is of particular importance if a very low temperature freezer (e.g. a −80° C. freezer) is used in sub-processes 2 and 3 of FIG. 7.

In a preferred embodiment where the freezer block 490 is used with a multi-pipetting robot like the Opentrons Flex OT-2 Workstation, the insulating pad 500 would be sized to fit in the opening for a standard 96 well plate and fit into a recess (not shown) in the bottom of the freezer block 490 to ensure alignment of the recess 495 with the recess in the base of the robot that ensures accurate pipetting of fluids into the wells shown in FIGS. 9A through 9C.

It is also envisioned that a larger freezer block designed to hold multiple production modules 480 of FIG. 8 could be produced to facilitate production of multiple sets of eight 12-well strips (or sixteen 4 well strips etc.) during each stage of the sub-processes 1 and 3 of FIG. 7

FIG. 11A is a graph showing an example of the luminescence data over time from a 12-well strip over ten minutes. Each dot represents the amplitude of the luminescence from one of the 12 wells being the number of photons detected from the well by a detection device (e.g. a plate reader) during the half second measurement period used to sequentially measure each well. For this example, the TET coupled enzyme assay strip (e.g., the strip 400 of FIG. 4A) has four sets of three wells along its length of with each set having a test well (e.g., the well 452T in FIG. 4C), a positive control well (e.g., the well 452P of FIG. 4C), and a negative control well (e.g., the well 452N of FIG. 4C). When placed into a standard plate reader such as the Tecan Infinite 200 PRO, each of the strip's 12 wells has its luminescence measured in turn again and again with all 12 wells read every 10 seconds for a 10 minute duration period by the light detector (e.g., a photomultiplier tube) in the plate reader.

Each dot represents the number of photons detected over the pre-set time period (e.g. 0.5 seconds) and with different shades of dots for each of the 12 wells as follows:
- 811L, 812L, 813L and 814L representing the luminescence from each of the four positive control wells,
- 821L, 822L, 823L and 824L representing the luminescence from each of the four test wells,
- 831L, 832L, 833L and 834L representing the luminescence from each of the four negative control wells.

The kinetics of the luminescence produced by the coupled enzyme assays of the present invention embodiments are such that the activity of the enzyme in the sample (e.g., NSE, ALT or AST) will be approximately proportional to the rate of the luminescence photon production (given as LU) per second. The rate of the light output (luminescence) is determined by the slope of each of the N, T, and P traces, with units of Luminescence Units (LU) per Second (LU/Sec).

Plate readers (e.g., the TECAN Infinite 200 Pro) include software that can calculate a linear slope from the data collected for each well's luminescence over a measurement portion of the duration period (e.g., 10 minutes in FIG. 11A). It is envisioned that this measurement period can be as short as 30 seconds and as long as 30 minutes with a preferred embodiment being 2-5 minutes. In a preferred embodiment, one would start the measurement period with an optional brief, pre-determined delay after the start of the assay, which commences upon addition of the fluid sample to the test, positive and negative control wells and insertion into the plate reader. For example, a 2 minute measurement period could begin 30 seconds after the start of the duration period.

FIG. 11A shows the 12 slopes calculated for each of the 12 wells and three average slopes as:
- 811S, 812S, 813S and 814S representing the luminescence slopes from each of the 4 positive control wells,
- 821S, 822S, 823S and 824S representing the luminescence slopes from each of the 4 test wells,
- 831S, 832S, 833S and 834S representing the luminescence slopes from each of the 4 negative control wells.
- average slope for the four positive control wells 815 ($S_P$),
- average slope for the four test wells 825 ($S_T$) and
- average slope for the four negative control wells 835 ($S_N$).

In a preferred embodiment the average slopes 815 ($S_P$), 825 ($S_T$) and 835 ($S_N$) are used by the plate reader to calculate the relative activity of the enzyme (e.g., NSE-FA) in the sample.

To understand how this works one begins with the contributions to the luminescence for each type of well. It is also important to note that the rate of the enzymatic activity in the coupled enzyme reaction of embodiments of the present invention is approximately proportional to the slope of the luminescence curve during a period of M minutes of the reaction before saturation effects occur. In embodiments, M may be between 1 and 30 minutes that optionally may start after a short delay. While the total kinetics of a coupled enzyme assay like that of the present invention are influenced by the various rates of activities of each enzyme, and subject to influences of changing concentrations of reaction products, substrates and cofactors, for the sake of simplicity here, the methods described herein are envisioned as a viable technique to reproducibly determine the activity of the enzyme biomarker E1 of FIG. 1.

Specifically:
1. Luminescence from a negative control well will be produced from any molecule in the blood that could activate either tethered enzyme in the coupled enzyme reaction or react with luciferin. As the initial substrates for the biomarker enzyme being assayed is missing, the luminescence data seen from the negative control wells 831L, 832L, 833L, and 834L will be the base luminescence of the test and positive control wells. If this is too high, it may signal an error condition that would require a re-test for example. In embodiments of the present invention, means to identify error conditions from the negative control data are envisioned,
2. Luminescence from a test well will equal that of luminescence from a negative control well plus the luminescence produced by the reaction of the substrates SA1 and SA2 with the active Enzyme E1 of FIG. 1. Thus the normalized value of the activity of the Enzyme E1 sample pipetted into a test well(s) $S_{TR}$ can be calculated by subtracting the luminescence slope $S_N$ of the negative control well(s) from $S_T$ of the test well(s).
3. Luminescence from a positive control well will include the luminescence from a test well (2 above) plus the luminescence produced by the additional enzyme pre-seeded in the test well in layer 462 of FIG. 4C. Thus the normalized value of the activity of the pre-seeded enzyme in layer 462 of FIG. 4C $S_{PR}$ can be calculated by subtracting the luminescence slope $S_T$ of the test wells from luminescence slope $S_P$ of the positive control well(s).

Mathematically, the Real luminescence slope $S_{PR}$ defined as the fraction of luminescence from only pre-seeded enzyme in the positive control well(s) (e.g., enolase for NSE-FA) can be calculated as:

$$S_{PR} = S_P - S_T \text{ and}$$

the Real luminescence slope $S_{TR}$ from the NSE-FA in the patient sample from the test wells defined as the fraction of luminescence from only the biomarker enzyme E1 of FIG. 1 in the sample added to the test well(s) can be calculated as:

$$S_{TR} = S_T - S_N$$

The values of $S_{PR}$ and $S_{TR}$ provide a means to not only measure the activity of the enzyme E1 of FIG. 1 in the patient sample (e.g., NSE-FA), but also provide a technique that can be used to set a threshold for setting a normal range for such activity (e.g., for significant brain injury for the NSE-FA coupled enzyme assay).

In a preferred embodiment, an Activity Level can be calculated where the Activity Level ($A_P$) is $S_{TR}$ expressed as percentage of $S_{PR}$ i.e.

$$A_P = 100 \times S_{TR}/S_{PR}$$

In terms of the slopes from the measured luminescence traces, this would be $$A_P = 100 \times (S_T - S_N)/(S_P - S_T)$$

It is also envisioned that a fraction $A_F$ may be used where $A_F = S_{TR}/S_{PR}$.

In another embodiment, the positive control and test well luminescence slopes may be normalized to the negative control only and the negative control normalized activity may be represented as a percentage or fraction as:

$$A_N = 100 \times (S_T - S_N)/(S_P - S_N),$$

or $$A_F = (S_T - S_N)/(S_P - S_N)$$

Whether a fraction or percentage, these normalized values of activity can be compared to a normal range of activity with lower bound $A_{TL}$ and upper bound Aru where detection of abnormal biomarker levels would be levels of activity below $A_{TL}$ or above $A_{TU}$.

In other embodiments, the 12 slopes may be used to reduce variance by taking the median of the slopes instead of the average or by eliminating the high and low and averaging the two other slopes to get the average slopes $S_P$, $S_T$ and $S_N$.

In still other embodiments, the 12 slopes may be used to reduce variance by removing any one slope that differs by more than some percentage (e.g., 5%) from the other three values.

While the term amplitude for FIG. 11A represents the number of photons detected over a half second by the reader used, it is envisioned that it can also be used in embodiments to represent any measurement of the amount of luminescence from a well or zone including:
1. the voltage at a specific time or the average voltage from a photodiode or
2. a counted number of photons by a photo multiplier tube in a luminescence reader.
3. the output from a charge coupled device at a single point in time or averaged over to pre-set time period.

FIG. 11B is a graph showing an alternate algorithmic embodiment using the Area Under the Curve ($AUC_P$, for the positive control wells, $AUC_T$ for the test wells and $AUC_N$ for the negative control wells) to measure luminescence data from a coupled enzyme reaction. Similar subtractive methods or other algorithms may be applied to these values over a preset duration period (e.g. ~10 minutes in FIG. 11B) to calculate the activity of the biomarker in the patient samples.

FIG. 11C is a graph showing an alternate algorithmic embodiment to measure luminescence data from a coupled enzyme reaction using the an average value of the luminescence ($P_P$ for the positive control wells, $P_T$ for the test wells and $P_N$ for the negative control wells) at point in time.

FIGS. 11B and 11C are alternatives to the scheme using slope described for FIG. 11A. These alternatives may be preferable for embodiments, for example, where the biomarker is a substrate and not an enzyme. These alternate embodiments of the present invention would include algorithms for measuring amounts of biomarker in a patient sample such as:

Measurement based on the area under the curves (AUC) as shown in FIG. 11B. Here calculations would be based on the values of the areas under the curves for the positive controls $AUC_P$, test wells $AUC_T$ and negative control wells $AUC_N$. FIG. 11B uses 600 seconds for this calculation but a longer or shorter time may be utilized. The calculation of the Real luminescence from the sample pipetted into the test wells $AUC_{TR}$ and Real luminescence from the biomarker pre-seeded in the positive wells $AUC_{PR}$ can be calculated similarly to that shown in FIG. 11A where: $AUC_{TR} = AUC_T - AUC_N$ and $AUC_{PR} = AUC_P - AUC_T$. The measured biomarker level can then be assessed as $AUC_{TR}$ as a percentage or fraction of $AUC_{PR}$.

Measurement based on the peak luminescence over a pre-set time period as shown in FIG. 11C (in this example, for a 10 minute (600 second) time period). Here a similar algorithm to that used for slopes on FIG. 11A or area under the curve for FIG. 11B can be implemented. For example, the calculation of the Real luminescence from the sample pipetted into the test wells $P_{TR}$ and Real luminescence from the biomarker pre-seeded in the positive wells $P_{PR}$ can be calculated similarly to that shown in FIG. 11A where: $P_{TR} = P_T - P_N$ and $P_{PR} = P_P - P_T$. The measured biomarker level can then be assessed as $P_{TR}$ as a percentage or fraction of $P_{PR}$.

Other viable envisioned embodiments would include using:
The average of multiple activity measurements based on slope taken at a multiplicity of time points.
Measurement of the second derivative of the luminescence data curves.
Measurement of time to a peak value of luminescence.
Various combinations of the above (for example Peak Luminescence X Slope)

FIGS. 12A, 12B, 12C and 12D show an embodiment of the top view of lateral flow blood separation filter paper embodiments of the present invention that would be applicable to a Point-of-Care (PoC) or home use assay using the present invention tethered enzyme technology. The configuration shown would be applicable to embodiments of assays for NSE-FA or liver enzyme ALT and AST activity as shown in FIGS. 1, 2, 3A, 3B and 3C.

Figures 12A, 12B, 12C:
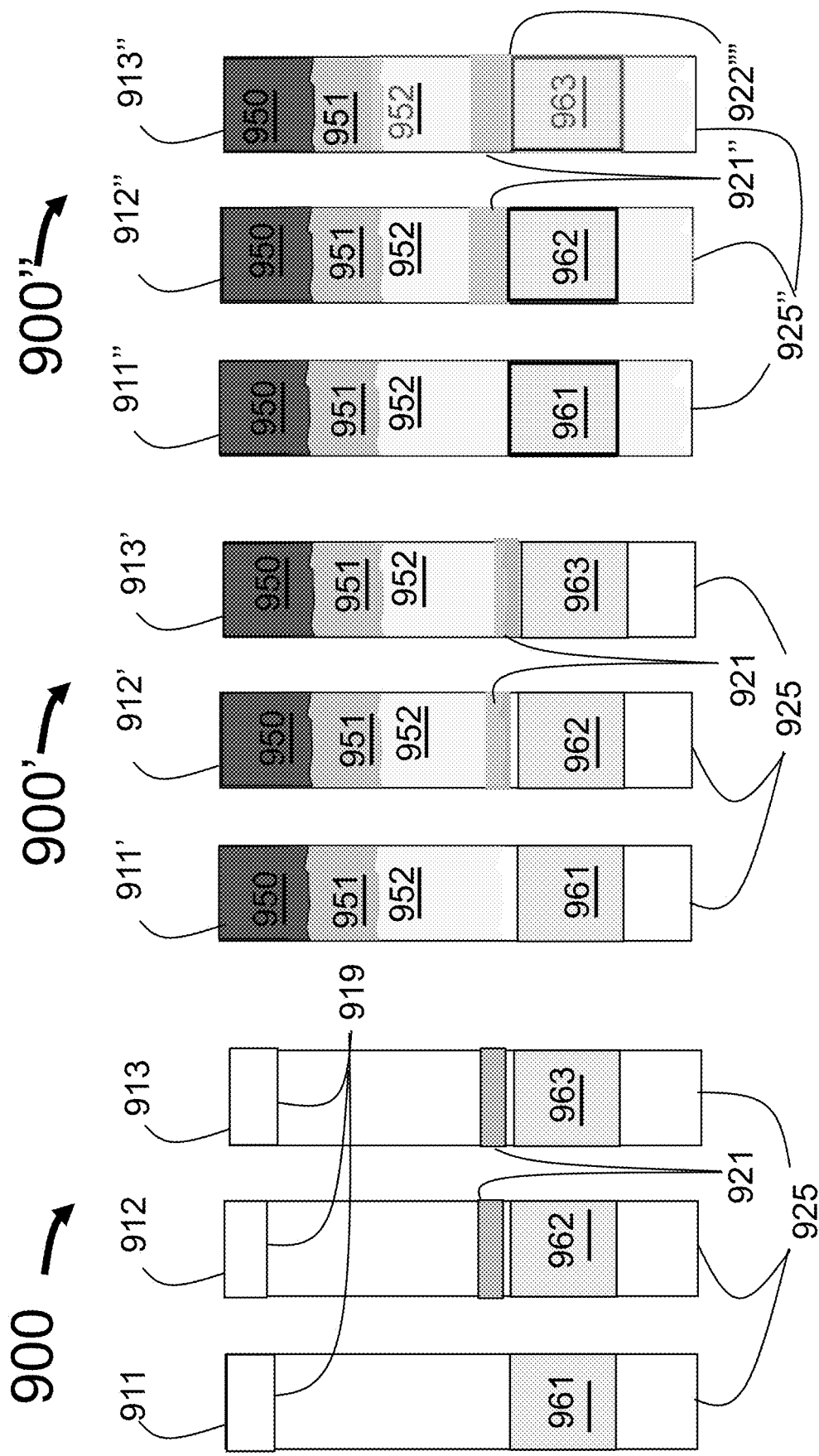
FIG. 12A is a top view showing the blood separation paper strip set with negative control strip, test strip and positive control strip as they might be configured before being used in a Point of Care (PoC) diagnostic assay.
FIG. 12B is a top view showing the strips at a time of several seconds after a patient's blood has been placed onto each of the three blood separation paper strips.
FIG. 12C is a top view showing the assay strips as the plasma has now filled the reaction zones and is filling the flow extension zones of the blood separation paper strips.

FIG. 12A is a top view showing the blood separation paper strip set 900 with negative control strip 911, test strip 912 and positive control strip 913 as they might be configured before being used in a PoC diagnostic assay.

A preferred embodiment of the strip set 900 would have well reaction zones 961 and 962 of strips 911 and 912 including components similar to layer 461 of FIG. 4C, and zone 963 of positive control strip 913 including the components similar to layer 462 of FIG. 4C including a preset amount of the assayed biomarker. The band 921 of strips 912 and 913 would have components similar to layer 463 of FIG. 4C including the substrate on which the enzyme biomarker works (for example, 2-PG for the NSE-FA coupled enzyme assay shown in FIGS. 3A and 3B). Fluid input zone 919 in strips 911, 912 and 913 shows the location where whole blood is placed. In a preferred embodiment the fluid input zone 919 may include or be connected to a blood absorbing reservoir or physical barrier that can help prevent overflow if excess blood is placed onto the zone 19.

In preferred embodiments, the entire strip may be sealed or coated except for the fluid input zones 919. Examples of such coatings include plastic and paraffin. A small air vent (not shown) could be added below the zones 925 to ensure full flow of the plasma into and past the reaction zones 961, 962 and 963. It is envisioned that once the liquid blood/plasma is fully saturated in the paper strip it will stop flowing with plasma in the reaction zones 961, 962 and 963 each having approximately the same amount of plasma that can react to provide luminescence.

In an embodiment, the flow extension zones 925 of strips 911, 912 and 913 allow excess plasma to flow beyond the reaction zones 961-963, ensuring that each reaction zone has a standard and saturating volume that fills the paper in that zone, but which does not pool in excess.

Other embodiments are envisioned that have the N, T, and P reaction on a single lateral flow paper, separated by hydrophobic separators such as ink or wax based. Rather than side-by-side, another embodiment might have the 3 lateral flow papers stacked over each other, with separation layer including photodiodes between the papers.

FIG. 12B is a top view showing the strips 900' at a time of several seconds after a patient's blood has been placed in the fluid input zone 919 of the strip set 900. It shows the blood in area 950 of the test strips 911', 912' and 913'. As the liquid flows away from the area 950, blood cells and cell fragments (e.g., platelets) are retained within the areas 950-951 and the remaining plasma 952 continues to flow down the strips 911', 912' and 913'. As shown the plasma has just reached the bands 921.

FIG. 12C is a top view showing the assay strips 900" as the plasma 952 has now filled the reaction zones 961, 962 and 963 and is filling the flow extension zones 925" of the strips 911", 912" and 913" respectively. As shown, the plasma 952 of the negative control strip reached the negative control reaction zone 961;

the plasma 952 of the reaction test strip has mixed with the band 921" bringing the reaction components and any products formed within the band 921" into the reaction test zone 962; and the plasma 952 of the positive control strip has mixed with the band 921" bringing the components and any products formed found in the band 921" into the reaction test zone 963.

The reaction zones 961, 962 and 963 will now produce luminescence that can be measured photometrically to provide the luminescence data such as that shown in FIG. 11A from which the activity of the enzyme E1 103 of FIG. 1 can be determined.

Examples for NSE-FA, ALT and AST of this preferred embodiment would have the following elements of FIG. 2 in the zones and bands of the strip set 900 as follows:

For NSE-FA, zones 961 and 962 would include the tethered enzymes Pyruvate Kinase (TET-PK) 303, tethered Luciferase (TET-Luciferase) 305 and the compounds ADP 302 and Luciferin 304 of FIG. 3A. The zone 963 would include the components in band 961 (or 962) plus a preset amount of enolase. In a preferred embodiment, the enolase would be tethered. The band 921 would include the substrate 2-PG 301 of FIG. 3A.

For ALT, zones 961 and 962 would include the tethered enzymes Glutamate Oxidase (TET-Glut-OX) and tethered Horse Radish Peroxidase (TET-HRP), and the compound Luminol shown in FIG. 2. The zone 963 would include the components in band 961 (or 962) plus a preset amount of the liver enzyme ALT. In a preferred embodiment, the ALT in zone 963 would be tethered. The band 921 would include the substrates α-ketoglutarate and L-Alaninine shown in FIG. 2.

For AST, zones 961 and 962 would include the tethered enzymes Glutamate Oxidase (TET-Glut-OX) and tethered Horse Radish Peroxidase (TET-HRP), and the compound Luminol shown in FIG. 2. The zone 963 would include the components in band 961 (or 962) plus a preset amount of the liver enzyme AST. In a preferred embodiment, the AST in zone 963 would be tethered. The band 921 would include the substrates α-ketoglutarate and L-Aspartate shown in FIG. 2.

In this embodiment pre-treatment of the blood or plasma with uricase (tethered or not) and uric acid is necessary for the ALT and AST luminescence coupled enzyme assays of the present invention. For liver enzyme use with the configuration of the strip set 900 of FIG. 12A, the blood would need be pre-treated before it is placed onto the strips 911, 912 and 913. In a preferred embodiment this pre-treatment uses freeze dried tethered uricase and uric acid placed into the blood collection vial from which blood is added to the strip set 900. This may be done by freeze drying the uric acid and uricase onto the inside surface of the vial or separately introducing them into the vial, for example by adding a tablet, or powder to the vial.

While it is possible to put all the components into the reaction zones 961, 962 and 963 using layering such as shown in FIG. 4C, an advantage of this preferred embodiment of the PoC assay is that the substrates with which the biomarker reacts in the band 921 are separated from the reaction zones 961, 962 and 963.

In embodiments of the present invention PoC coupled enzyme assay, it is envisioned that a single input of blood could be configured with the fluid input zones 919 of the negative control strip 911, test strip 912 and positive control strip 913 interconnected so that blood placed in the interconnected zone 919 would flow and be filtered into 3 or more blood filter/assay strips or channels such as the strips 900. Examples of this concept are shown in FIGS. 13A, 13B and 14.

For clarification, the term band such as the bands 921 of FIG. 12A refers to a collection of components meant to be picked up by fluid (e.g. plasma) flowing down the strips 912 and 913 such that those components are carried into the reaction zones 962 and 963 where they participate in any reaction producing assay luminescence. The reaction zones 961, 962 and 963 are the areas of the strips 911, 912 and 913 monitored by photon detection mechanisms adapted to measure the amplitude of the luminescence reaction occurring in each reaction zone.

Figures 12D, 12E:
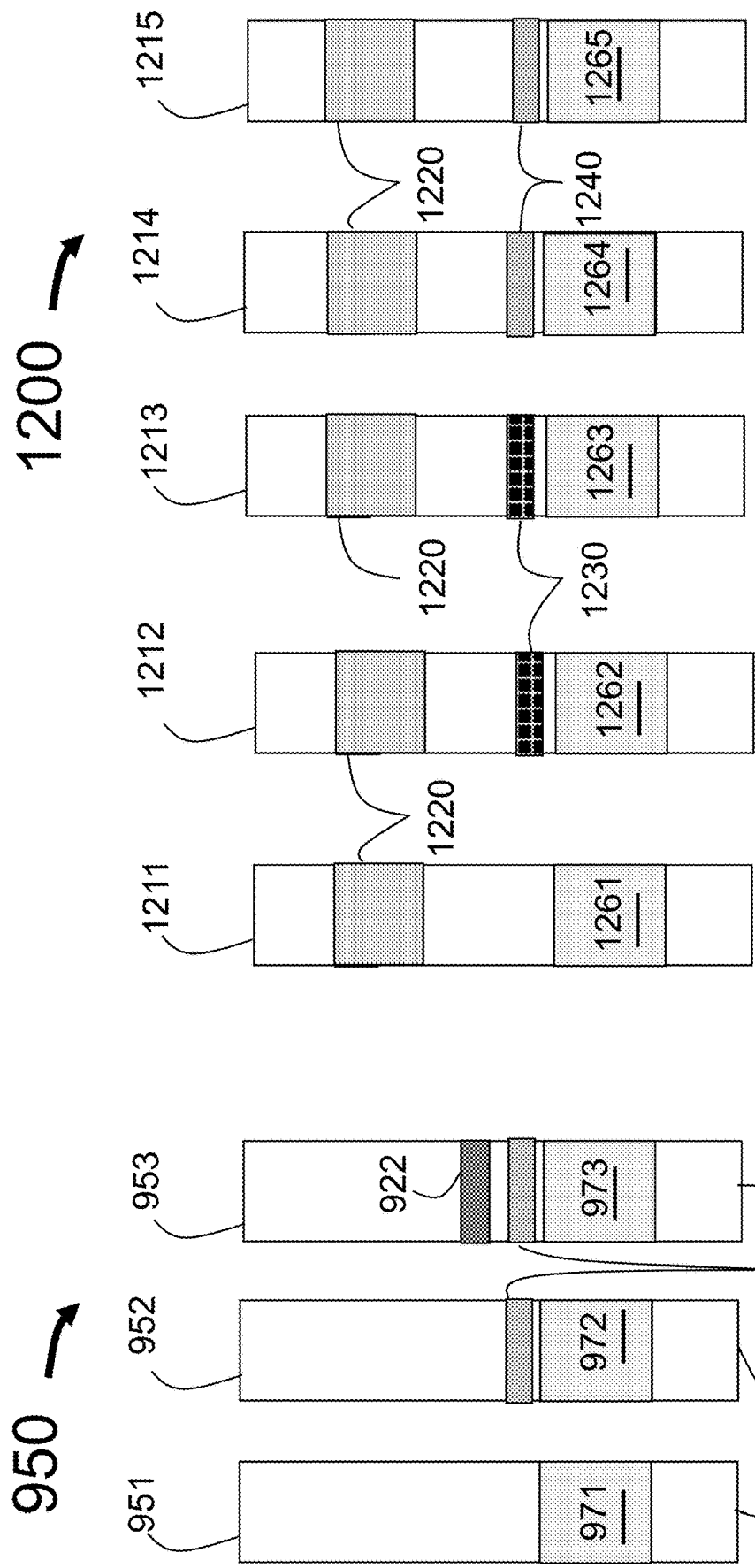
FIG. 12D is a top view showing an alternate embodiment of the lateral flow blood separation paper strip set.
FIG. 12E is a top view showing the blood separation paper strip set for both liver enzymes ALT and AST as they would be configured before being used in a PoC diagnostic assay.

FIG. 12D is a top view showing an alternate embodiment of the lateral flow blood separation assay paper strip set 950 with negative control strip 951, test strip 952 and positive control strip 953. In this embodiment, this negative control strip 951 is the same as the negative control strip 911 of FIG. 12A and the test strip 952 is the same as the test strip 912 of FIG. 12A. Specifically, the zone 971 is the same as the zone 961 of FIG. 12A, the zone 972 is the same as the zone 962 of FIG. 12A, the band 971 is the same as the band 921 of FIG. 12A and the area 975 is the same as the area 925 of FIG. 12A.

While the band 974 of the positive control strip 953 is the same as the band 921 of FIG. 12A, the positive control strip 953 differs in that the components in the zone 973 has the same components as the zones 971 and 972 and does not include a preset amount of biomarker as does the zone 963 of FIG. 12A. In this embodiment, the preset amount of biomarker is placed into band 922 that will release the biomarker into the flowing plasma as it flows down strip 953 similar to the flow of plasma in FIGS. 12B and 12C.

FIG. 12E is a top view showing the blood separation paper strip set 1200 for both liver enzymes ALT and AST with negative control strip 1211, ALT test strip 1212, ALT positive control strip 1213, AST test strip 1214 and AST positive control strip 1215 as they would be configured before being used in a PoC diagnostic assay.

The zones 1261, 1262 and 1264 include the tethered enzymes (see FIG. 2) TET-Glut-Ox, TET-HRP as well as Luminol for the ALT/AST liver tests. Zone 1263 also includes the pre-set amount of ALT (tethered or not) as the positive control for the ALT assay. Zone 1265 also includes a pre-set amount of AST (tethered or not) as the positive control for the AST assay.

The bands 1230 of strips 1212 and 1213 include α-ketoglutarate and L-Alanine, the substrates with which ALT reacts. The bands 1240 of strips 1214 and 1215 include α-ketoglutarate and L-Aspartate, the substrates with which AST reacts.

It is also envisioned that in embodiments, the positive control pre-set amounts can be in a separate band like the band 922 of FIG. 12D instead of in the zones 1263 and 1265 of FIG. 12E.

The embodiments of ALT and AST assays in FIG. 12E do not require separate pre-treatment of the blood in a separate vial but include the bands 1220 having uric acid and uricase (tethered or not) that will provide the pre-treatment as the blood and then plasma flow along the strips 1211 through 1215 so that the treatment will be completed before the plasma reaches the zones 1261 through 1265.

While the preferred embodiment of positive controls uses a preset amount of the biomarker being assayed (or an analog such as enolase for NSE), it is envisioned that alternate positive control formulations the include pre-set amounts of substrates/intermediates produced in later portions of the coupled enzyme reaction would function well. For example, for the NSE-FA assay, having a pre-set amount of phosphoenolpyruvate (PEP) made by NSE-FA or ATP could function rather than a preset amount of enolase.

It is envisioned that instead of the paper chromatography strips shown in FIGS. 12A through 12D, for the purposes of this specification, the present invention embodiments of fluid flow strips may include any fluid flow entity (with or without blood separation capability) selected from the group of:
chromatography paper,
microfluidic channels,
membranes,
matrices, or beads/particles/fibers
any fluid flow entity in an enclosed space that will facilitate passive fluid flow (e.g., as achieved through capillary action), or active flow (e.g., as achieved with a pump).

For the purposes of this specification, the term test strip may represent any of the above types of fluid flow entity with a test zone designed to measure a biomarker, a positive control strip may represent any fluid flow entity that has a pre-set amount of the biomarker to allow the assay to quantify the amount of biomarker or biomarker activity in the sample, and the term negative control strip represents any fluid flow entity that can serve as a negative control for the present invention assay.

FIG. 13A is a schematic view showing an embodiment of a TET assay card 1200 configured for insertion into a photodiode-based reader. The assay card 1200 has a main body 1201, handle 1202 and assay structure 1250 having a fluid input zone 1210, blood separation strip 1221 and plasma flow structures 1215, 1216, and 1217 with 1215 connected to the test zone 1211T, 1216 connected to the negative control zone 1211N and 1217 connected to the positive control zone 1211P.

The plasma flow structures 1215 and 1217 have substrate bands 1231 similar to the bands 921 of FIG. 12A and the bands 974 of FIG. 12D. The plasma flow structure 1217 also has a positive control band 1232 has a preset amount of the biomarker being assayed similar to the band 922 of the positive control strip 953 of FIG. 12D. In this embodiment, the materials in zone 1211T are similar to that of zone 972 of FIG. 12D, the contents of the zone 1211N are similar to that of zone 971 if FIG. 12D and the contents of zone 1211P are the same as the that of zone 973 of FIG. 12D.

In a preferred embodiment, the band 1232 is missing and like the embodiment of FIG. 12A, the pre-set amount of biomarker is included in zone 1211P similar to that of zone 963 of FIG. 12A.

In this preferred embodiment where the positive control zone 1211P includes a pre-set amount of biomarker, the operation of the card 1200 is similar to that shown with the strip sets 900' and 900" of FIGS. 12B and 12C where blood cells and cell fragments are restrained within the blood separation strip 1221 allowing plasma to flow down the plasma flow structures 1215, 1216 and 1217 picking up materials in the substrate bands 1231 (test and positive controls only) and flowing into the reaction zones 1211T, 1211N and 1211P respectively.

In use, the card 1200 would be removed from its sealed and light proof pouch, blood from a finger prick or point of care collection device would be placed into the fluid input zone 1210 and the card 1200 held by the handle 1202 would be placed into a photodiode detection device where insertion would, in a preferred embodiment, activate or turn on the device that would then analyze the luminescence from the three reaction zones 1211T, 1211N and 1211P to provide a quantitative measurement of the biomarker and/or indicator of the test result as being one or more of: high, low and/or negative or positive.

For example, NSE-FA that exceeds a threshold would indicate significant acute brain injury that might be associated with a stroke or concussion. Note that the indicator could have various embodiments, including visual displays (e.g., text saying "high" versus "normal," or one or more colored lights such as green for normal range values, versus red for high values), or an auditory indicator for values exceeding the threshold, or any combination thereof.

FIG. 13B is a top view showing an embodiment of a TET diagnostic PoC card layout 1300 where the fluid input zone 1320 is centrally located with 5 blood separation strips 1311, 1312, 1313, 1314 and 1315 leading to reaction zones 1301, 1302, 1303, 1304 and 1305 respectively. Substrate bands 1321, 1322, 1323 and 1324 can have components or function similar to that of the bands 921 of FIG. 12A.

Embodiments of the card 1300 could have any combination of test, positive control and negative control reaction zones; however, a preferred embodiment would have one negative control zone, one positive control zone and three test reaction zones.

In a preferred embodiment such as that for liver enzymes ALT and AST, one could have a configuration where the 5 strips would have similar function to the 5 strips of FIG. 12E with zone 1301 being the test zone for ALT, 1302 the positive control for ALT, 1303 being the test zone for AST, 1304 being the positive control zone for AST and 1305 being the negative control zone. This configuration would use the blood pre-treatment method in a collection vial of FIG. 3C. An alternate embodiment would include an added band or area for pre-treatment in or near the fluid input zone 1320.

FIG. 14 is a schematic view of an embodiment of a TET coupled enzyme assay test module 1400 where a blood sample volume 1450 is deposited into the upper cylinder 1420 with strip holder 1411 and 4 blood separation paper strips 1451, 1452, 1453 and not shown 1454 having fluid input zones 1481, 1482, 1483 and 1484 (not shown). The strip 1452 is the test strip with the substrate band 1462 and reaction zone 1472 similar to the strip 912 with band 921 and reaction zone 962 of FIG. 12A. In an embodiment, a valve 1404 with actuator 1406 would allow blood to be placed in the upper portion 1490 of the upper cylinder 1420 to control the start of blood flow into the strips 1451, 1452, 1453 and 1454 (not shown). In embodiments, a portion of the actuator 1406 lies outside of the upper cylinder 1420.

The strip 1451 is a negative control strip with reaction zone 1471 similar to the strip 911 with reaction zone 961 of FIG. 12A. Optical separation is important for an accurate reading of luminescence. To facilitate that, the test module 1400 includes optically opaque separators 1441 and 1442 with two not shown 1443 and 1444. The allows the module 1400 to be inserted into a photodiode-based optical reader such as that shown in FIG. 16 where at least one photodiode is aligned with each reaction zone e.g. 1471,1472 etc., to have each photodiode accurately measure the luminescence from each zone and with electronic circuitry, that may include a microcomputer, analyze the results using an activity measurement calculation such as those described in association with FIGS. 11A, 11B and 11C.

The module 1400 can be used in several ways. In some embodiments it may be a stand-alone fully disposable device with an integrated reader with blood inserted from a syringe, vacuum collection tube, or other devices used to collect blood from venipuncture or a finger prick, or be set to be attached as a microtainer to a blood collection device such as the TASSO of Tasso, Inc.

In a preferred embodiment, the module 1400 can be designed to be inserted into a photodiode-based reader where only the module 1400 need be disposable.

Although four reaction zones 1471-1474 are described here, as few as one and as many as twenty zones or more may be used with a preferred embodiment of three or four zones.

The flow extension zones 1475,1476, and not shown 1477 and 1478 perform the same function as the flow extension zones 925 of FIG. 12A.

It is also envisioned that each of the strips 1451, 1452, 1453 and 1454 except for the fluid input zones 1481, 1482, 1483 and 1484 could be coated with a sealing material, e.g., plastic or paraffin. This will cause the plasma to flow down each strip 1471-1474 and stop once the filter paper is fully saturated. A small air vent may also be added to the bottom of the sealed strips 1451, 1452, 1453 and 1454. Similar coatings are also applicable to the embodiments shown in FIGS. 13A, 13B, 13C, 15 and 16.

FIG. 15 is a schematic view of an embodiment of a two-piece TASSO/TET assay system 1500 with a Photonic Luminescence Reader (PLR) 1550 and the TASSO blood collection device 1510 with initiation button 1512 and with the normal collection vial replaced by an embodiment of the TET coupled enzyme assay test module 1520 similar to the test module 1400 of FIG. 14 but with the addition of the alignment key 1525. The test module 1520 is designed to receive the blood collected by the TASSO device 1500, separate the cells from the plasma allowing the plasma to flow along the four strips 1521,1522, 1523 and 1524 (not shown) into the reaction zones 1531, 1532 and 1533 and 1534 (both not shown), picking up where needed chemicals in for example the substrate band 1542 of the test strip 1522.

The Photonic Luminescence Reader (PLR) 1550 with upper case 1552 includes an alignment female key slot 1582 as part of the generally cylindrical guide 1580. The guide 1580 has four attached photodiodes 1591, 1592, 1593 and not shown 1594 with cables 1595, 1596, 1597 and not shown 1598 to attach the photodiodes to electronic circuitry in the electronics module 1570. Each of the cables 1591-1594 has typically one or two wires each. The photodiodes 1591-1594 are attached to the cylindrical guide 1580 with at least the portion of the guide 1580 where the photodiodes 1591-1594 are attached being optically transparent. This can be accomplished by different embodiments including having a hole in the guide 1580, having the entire guide 1580 be transparent or in a preferred embodiment, having a transparent window under a portion of the photodiodes 1591, 1592, 1593 and not shown 1594. Embodiments with holes or windows may be preferred to prevent light leakage from one zone being detected by a photodiode aligned with another zone (i.e. crosstalk).

The PLR 1550 has an electronics module 1570 attached to the bottom of the upper case 1580 into which the cables 1595-1598 bring the signals from the photodiodes 1591-1594 to the electronic circuitry with an embodiment shown in FIG. 17. The outside of the PLR also includes a start button or switch 1572, a digital readout 1576 and an indicator LED 1574. The digital readout 1576 provides information on the quantitative measurement of the assay performed by the PLR 1550 with the LED 1574 being able to indicate one or more detection related conditions. For example, the LED 1574 might be red/green/yellow LED where it would be green if detection of NSE-FA is below the threshold for brain injury and red if above. It might flash while the device is working and could go yellow for an error condition. As noted above, other indicators including auditory could be present in different embodiments. In an embodiment of the present invention module 1520, strip 1521 is the negative control strip, strip 1522 is the test strip and strip 1523 is the positive control strip. In an embodiment, the $4^{th}$ strip 1524 that is hidden behind the schematic view, can be one of the following:

- An additional test strip
- An additional positive or negative control strip
- An additional biomarker assay test different from that of the test strip 1522, for example for the NSE-FA assay a test that includes an inhibitor for Neuron Specific Enolase and allow luminescence from other types of enolase in the sample. Another example for liver enzymes is to have strip 1522 be for ALT and strip 1524 for AST with a common negative control (or positive control) for comparison.

It is envisioned that multiple digital displays or LEDs might also be used with configurations that could include indication of power on, negative result, positive result, error condition, test working and/or numerical or alphanumerical displays. Embodiments of the electronics module 1570 having wireless or wired telemetry as shown in FIG. 17 is also envisioned.

One embodiment of the method for using the system 1500 for detecting and measuring acute brain injury is as follows:
1. The TASSO device 1510 is removed from its package
2. The TET module 1520 is attached to the TASSO device 1510 in place of the normal container;

3. The TASSO is placed on the patient's arm, the central button 1512 is pressed to initiate blood collection;
4. After a pre-set time (e.g. 2-5 minutes) or when the blood fills the TET module 1520 to a marked level, the entire TASSO 1510 or just the module 1520 is removed from the patient and inserted into the PLR 1550 aligning the key 1525 of the module 1520 with the slot 1582 of the PLR 1550.
5. The start button 1572 is pressed and the electronic circuitry of the electronics module 1570 will collect luminescence data from the 4 photodiodes 1591-1594 for a pre-set period.
6. The electronics module 1570 will then calculate the enzymatic activity of the biomarker being assayed and show the result on the numerical display 1576. For example embodiments of example calculations are described along with FIGS. 11A, 11B and 11C.
7. The electronics module 1570 would also compare the value of the activity with a pre-set threshold and turn the LED 1574 red if above the threshold and green if below.
8. The TASSO 1510 with module 1520 are then disposed of. The PLR 1550 will turn off after the module 1480 is removed to be available for another reading.

It is also envisioned that a contact switch (not shown) could be added to the top of the electronics module 1570 activated when the module 1520 is inserted into the electronics module 1570 to automatically turn the electronics on, eliminating the need for the switch 1572. The contact switch may be located at different places with a preferred embodiment requiring that it activate once the reaction zones e.g. 1531 and 1532 align with the photodiodes 1591 and 1592 respectively.

FIG. 16 is a schematic view of an integrated and fully disposable point-of-care TET coupled enzyme assay system 1600 including a TASSO blood collection device 1510 with initiation button 1512. The standard TASSO blood collection vial is replaced by the TET coupled enzyme assay test module 1680 similar to the TET module 1520 of FIG. 15 or the TET module 1400 of FIG. 14. The TET module 1680 includes the test 1672, positive control 1673 and negative control 1671 blood filtration strips similar to the strips 1522, 1523 and 1521 respectively of the module 1520 of FIG. 15 but the module 1680 also includes the cylindrical housing 1690 with photodiodes 1691,1692 and 1693 similar to the cylinder 1580 and photodiodes 1591, 1592 and 1593 of the separate PLR 1550 of FIG. 15. The photodiodes 1691, 1692, 1693 and 1694 (not shown) with cables 1695, 1696, 1697 and 1698 (not shown) perform the same function as the photodiodes 1591-1594 and cables 1595-1598 of FIG. 15.

The integrated assay 1600 has an electronics module 1670 attached to the bottom of the upper detection module 1690 into which the wires 1695-1698 bring the signals from the photodiodes 1691-1694 to the electronic circuitry. An embodiment of such electronic circuitry is shown in FIG. 17.

Operation of the system 1600 can be similar to that of the system 1500 of FIG. 15 with the TASSO 1510 button 1512 initiating both the collection of blood and the activation of the electronics module 1670 to measure the luminescence from the reaction zones (hidden) in the TET module 1690. The result is a qualitative and quantitative measurements of the assay shown by the color on the LED 1674 and numerically on the display 1676 respectively.

The two-piece embodiment is preferred if multiple tests need to be performed where the TASSO/TET 1510/1480 modules are disposable and the PLR 1550 is multi use. For single assay use such as for concussion at a football game, the fully disposable integrated PoC unit 1600 would be the preferred embodiment.

FIG. 17 is a block diagram of an embodiment of the electronics module 1700 that has features that would be incorporated into either or both electronic module embodiments 1570 of FIG. 15 and 1670 of FIG. 16. The module 1700 has a battery 1770, up to N photodiodes PD1 1701, PD2 1702, PD3 1703 through PDN 1704 whose signal is amplified and/or filtered through the amplifiers 1711, 1712, 1713 through 1714 whose output is digitized by the analog-to-digital converter(s) 1720. The digital signal is sampled into FIFO buffer memory 1730 and input to the central processing unit (CPU) 1740 with the A-to-D converter(s) 1720, FIFO Memory 1730 and CPU 1740 synchronized by the clock/timing sub system 1750.

In some embodiments, the CPU 1740 has one or more buttons/switches 1747 such as the start button 1572 of FIG. 15 or may receive input from depression of the TASSO button 1512 of FIGS. 15 and 16. The CPU 1740 also has assay data memory 1741, program memory 1742, and connects to a telemetry sub-system 1760 with Antenna 1765.

The telemetry subsystem 1760 with antenna 1765 may be configured to operate using a standard wireless protocol, for example: Bluetooth, WiFi or Medical Band (MICS). An embodiment of the telemetry sub-system 1760 may also provide a wired connector 1762 (e.g. USB, USB-C, lightning or other) to connect the system 1700 to a local computer, tablet or smart-phone (e.g. iPhone or Android).

In embodiments with a separate assay module/card and electronic module such as the configuration shown in FIG. 15, the electronics module may include a bar code reader 1749 to record the serial number of the assay module/card used in the assay that can be transmitted to external equipment using the telemetry sub-system 1760.

Also connected to the CPU is a temperature sensor 1748 whose reading may be used by the CPU 1740 to adjust parameters in the biomarker detection calculation for a TET assay that may be affected by temperature.

The output of the detection and measurement calculation(s) in the CPU 1740 can be displayed with the alpha-numeric display 1745 or the LED(s) 1746, or an auditory signal (not shown).

FIG. 18 is a schematic view showing a preferred embodiment of a point of care blood collection device 1500 such as the TASSO® with body 1510 and blood collection activator 1512. A blood collection vial/microtainer 1820 shown with collected blood 1830 and bottom surface 1825 suitable for needle penetration.

In embodiments, the microtainer 1820 has specific materials inside that can be used to pre-treat the blood (for example, the uricase and uric acid shown as A0 101 in FIG. 1. In embodiments, such materials may be freeze died and attached to the inner surface of the microtainer 1820 or simply placed into the microtainer 1820 as a powder or tablet.

FIG. 19 is a schematic view showing a preferred embodiment of a disposable NSE coupled enzyme reaction functional activity stroke test (NSE-FAST) assay 1900. The use of the assay 1900 is similar to that of the Lucira® Covid test sold by Pfizer. The embodiment of the assay 1900 has a case 1920, a numerical display 1905 and four LEDs including a ready LED 1902, a done LED 1904, a positive test LED 1906 and a negative test LED 1908. The assay 1900 has a cylindrical slot 1920 for insertion of the microtainer 1820 with bottom surface 1825 of FIG. 18. At the bottom of the slot 1920 (not shown) is a needle to puncture the bottom surface 1825 of the microtainer 1820 to allow blood 1830 to flow into the assay 1900 where blood separation paper strips similar to the blood separation paper strip set 900 shown in FIG. 12A with negative control strip 911, test strip 912 and positive control strip 913 would be used to separate out plasma that would then flow the into reaction zones similar to those shown in FIG. 12A, 13A, or 14A. Photo diodes (not shown) similar to the photo diodes 1701 through 1703 of FIG. 17 would sense the luminescence for test, positive control and negative control reaction zone(s) and the CPU 1740 of FIG. 17 would then calculate the activity of the enzyme in the patient sample as previously described. The CPU 1740 would then display the result using the numerical value 1905 and/or the test result positive LED 1906 or test result negative LED 1908. It is also envisioned that the assay 1900 may also utilize embodiments shown in FIG. 13A, 13B or 13C.

In embodiments, in addition or instead of the display it is envisioned that the CPU 1740 of FIG. 17 would transmit the result (measurement and/or positive/negative) to external equipment (not shown) through the telemetry sub-system 1760 over the wired connector 1762 or antenna 1765 of FIG. 17.

Similar to the Lucira® Covid test, although not shown, the bottom of the case 1920 could have a battery cover 1910 into which one or more batteries (e.g. the battery 1770 of FIG. 17) can be inserted to start the electronics running in preparation for the test. Alternately, the battery could be embedded and the insertion of the microtainer 1820 could turn the system on.

An embodiment of the present invention assay 1900 shown in FIG. 19 is envisioned for tethered enzyme PoC applications for many different biomarkers including the NSE-FA assay and ALT & AST liver enzyme assays shown in FIG. 2.

Also, while the example for FIG. 19 shows use with whole blood from a TASSO device, it is envisioned that the microtainer 1820 can be filled with plasma, serum, urine or liquid into which material from a nasal swab or other material is dissolved to facilitate detection of different biomarkers.

It is envisioned that for assays of liver enzymes ALT and AST the embodiment of the assay 1900 would have separate displays and positive and negative LEDs for each with a preferred embodiment using five blood separation chromatography strips like the strips 1200 of FIG. 12E if the pre-treatment bands 1220 are on the strip or like the strips 900 of FIG. 12A if the pre-treatment materials are in the microtainer 1820.

Throughout this specification we describe use of freezing and freeze-drying as important to the present invention as these will prevent premature activation of chemical reactions. It is envisioned that other methods can be used to also prevent premature activation of the chemical reactions described herein and embodiments using these other methods may also facilitate production of the present invention assays. Examples include manipulations of the combination of pressure and temperature, using powdered components including enzymes and the use of reaction inhibitors or dissolvable physical barriers between layers. Another technique envisioned is using encapsulated or caged components to prevent premature mixing of components. A final version is to utilize magnetic particles that can remain separated until the field is removed.

While the well versions of the present invention coupled enzyme assays are intended for use with plate readers capable of measuring luminescence, it is envisioned that small dedicated devices could be implemented to measure the luminescence from the wells using photo-diodes, CCD arrays, photomultiplier tubes or any other photon detection or measurement device.

While the present invention embodiments of the point-of-care assays show the use of photodiodes, embodiments using other photon detection or measurement devices including CCD arrays and photomultiplier tubes are envisioned.

While the present invention specification describes assays for Neuron Specific Enolase, these embodiments are equally appropriate and are applicable to an assay for any active enolase enzyme.

Various other modifications, adaptations, and alternative designs are of course possible in light of the above teachings. Therefore, it should be understood at this time that, within the scope of the appended claims, the invention can be practiced otherwise than as specifically described herein.

What is claimed is:

1. A coupled enzyme reaction point of care assay system for detection and measurement of an active enzyme biomarker present in a sample of the blood of a patient, the system comprising:
   a blood collection vial including pre-treatment materials adapted to remove anti-oxidants from a collected blood sample, the materials selected from at least one of the group including: uric acid and uricase, ascorbate oxidase and ascorbic acid, or glucose oxidase and glucose;
   a point of care blood collector for collecting a patient's blood into a blood collection vial;
   a biomarker detection mechanism comprising at least three fluid flow entities, each fluid flow entity having a fluid input zone and a corresponding reaction zone, and a blood insertion member for placing a preset amount of said blood from the blood collection vial onto each of said fluid input zones, each fluid flow entity adapted to provide for the flow of fluid from each fluid input zone to the corresponding reaction zone, at least one fluid flow entity being a test strip, at least one fluid flow entity being a negative control strip and at least one fluid flow entity being a positive control strip, the test strip and positive control strip each including a band located between the fluid input zone and the reaction zone, the band comprising a multiplicity one or more substrates with which the active enzyme biomarker will react, the test strip and positive control strip being adapted to facilitate the fluid flowing from each strip's fluid input zone to its reaction zone to carry the one or more substrates in the band into the corresponding reaction zone, each reaction zone of each fluid flow entity comprising a multiplicity of components, said components comprising: (i) a multiplicity of one or more types of substrates, co-factors, buffers and cryoprotectants, (ii) a multiplicity of at least two types of tethered enzymes each of the at least two types of tethered enzymes comprising at least 100 enzyme molecules tethered to a nanoparticle, each of the at least 100 enzyme molecules of the first type of tethered enzymes adapted to react to a reaction product formed from a reaction between the biomarker with the one or more other substrates in the band where present,
   the positive control strip also including a pre-set quantity of the enzyme biomarker; and
   a photonic luminescence reader adapted to measure an amplitude of light emitted from each of the reaction zones, the photonic luminescence reader including electronics adapted to calculate a measurement of an active enzyme biomarker present in the sample of the blood of a patient from the measurements of light amplitude from the reaction zones.

2. The system of claim 1 including a means within each of the at least fluid flow entities adapted to separate plasma or serum from blood collected by the point of care blood collector.

3. The system of claim 1 further where the one or more substrates of the band on each of the test strip and the positive control strip, comprises one or more component selected from the group comprising: a-ketoglutarate, L-Aspartate, L-Alanine, Uric acid, and Uricase.

4. The system of claim 1 where at least one type of tethered enzyme includes more than 1,000 enzyme molecules tethered to each nanoparticle.

5. The system of claim 1 where at least one of the fluid flow entities that will facilitate a fluid flow in an enclosed space is selected from the group of: chromatography paper, micro-fluidic channels, membranes, and matrices, or beads/particles/fibers.

6. The system of claim 5 where the fluid flow is passive flow.

7. The system of claim 5 where the fluid flow is active flow.

8. The system of claim 1 where the biomarker is selected from the group of: Alanine transaminase (ALT), and Aspartate transaminase (AST).

9. The system of claim 1 where the one or more types of substrates in the reaction zone are selected from the list group comprising: Luciferin, a-ketoglutarate, luminol, L-Aspartate, L-Alanine, Pyruvate, Oxaloacetate, and Uric acid.

10. The system of claim 1 where the enzyme molecule chosen for at least one of the one or more tethered enzyme molecules is selected from the group of: Alanine transaminase (ALT), Aspartate transaminase (AST), Pyruvate kinase, Luciferase, Glutamate Oxidase, Horseradish Peroxidase, and Uricase.

11. The system of claim 1 where the blood collection vial has a bottom surface that is puncturable by a needle.

12. The system of claim 1 where the nanoparticles are selected in a size range selected from at least one of the group of: 1 nm to 500 nm, and 500 nm to 1,000 nm.

13. The assay of claim 1 where the nanoparticles are selected from at least one of the group comprising: silica, polycarbonate, acrylics, reflective materials including silver, gold, platinum, and ceramics.

* * * * *